US008771652B2

(12) United States Patent
Labuda et al.

(10) Patent No.: US 8,771,652 B2
(45) Date of Patent: Jul. 8, 2014

(54) METHODS OF BLOCKING ULTRAVIOLET RADIATION AND PROMOTING SKIN GROWTH USING TERPENES AND TERPENOIDS (75) Inventors: Ivica Labuda, Norwood, NJ (US); Fredric Jay Burns, Ho-ho-kus, NJ (US)

(73) Assignees: New York University, New York, NY (US); Biokeys for Flavors, LLC, Norwood, NJ (US)

( * ) Notice: Subject to any disclaimer, the term of this patent is extended or adjusted under 35 U.S.C. 154(b) by 123 days.

(21) Appl. No.: 12/807,979

(22) Filed: Sep. 17, 2010

(65) Prior Publication Data
US 2011/0158921 A1 Jun. 30, 2011

Related U.S. Application Data (60) Provisional application No. 61/276,887, filed on Sep. 17, 2009.

(51) Int. Cl.
*A61K 8/00* (2006.01)
(52) U.S. Cl.
USPC ............ 424/59; 514/691; 514/690; 514/763; 568/374; 568/377
(58) Field of Classification Search
None
See application file for complete search history.

(56) References Cited

U.S. PATENT DOCUMENTS

| | | | |
|---|---|---|---|
| 4,387,089 A | 6/1983 | De Polo | |
| 4,603,146 A * | 7/1986 | Kligman | 514/559 |
| 4,784,842 A | 11/1988 | London et al. | |
| 5,614,197 A | 3/1997 | Pathak et al. | |
| 7,247,714 B2 | 7/2007 | Kunsch et al. | |
| 7,351,739 B2 | 4/2008 | Ho et al. | |
| 2004/0005342 A1 | 1/2004 | Bernerd | |
| 2004/0146587 A1 | 7/2004 | Spicer | |
| 2005/0058611 A1 | 3/2005 | Fagot et al. | |
| 2005/0281761 A1 | 12/2005 | Detmar et al. | |
| 2006/0073222 A1 | 4/2006 | Arntzen et al. | |
| 2007/0071839 A1 | 3/2007 | Bombardelli | |
| 2008/0014156 A1 | 1/2008 | Horn | |
| 2008/0286217 A1 * | 11/2008 | Chaudhuri | 424/59 |
| 2009/0036545 A1 | 2/2009 | Chaudhuri | |
| 2010/0305214 A1 * | 12/2010 | D'Alessio | 514/729 |

OTHER PUBLICATIONS

Luria-Prevatt et al ("Effects of Perillyl Alcohol on Melanoma in the TPras Mouse Model," Cancer Epidemiology, Biomarkers & Prevention vol. II. 573-579. Jun. 2002).*
Barthelman, et al., Cancer Research, 58, 711-716 (1998).
Aqil et al., "Status of Terpenes as skin penetration enhancers", Drug Discovery Today (2007) 12(23-24): 1061-1067.
Borek, "Dietary antioxidants and human cancer" Integrative Canc. Therapies (2004) 3(4): 333-341.
Burke et al., "Inhibition of pancreatic cancer growth by the dietary isoprenoids farensol and geraniol", Lipids (1997) 32(2): 151-156.
Candi et al., "The Cornified Envelope: A Model of Cell Death in the Skin", Molecular Cell Biology (2005) 6: 328-340.
Craig, "Heterogeneity of biochemical, clinical and immunological parameters in sever combined . . . ", American J. Clinical Nutrition (1999) 70(3): 491-499.
Crowell et al., Chemo prevention of mammaary carcinogenesis by hydroxylated . . . , Carcinogenesis (1992) 13(7): 1261-1264.
Crowell et al., "Identification of metabolites of the antitumor agent d-limonene capable . . . " Cancer Chemother. Pharmacol. (1992) 31: 205-212.
Crowell, et al., "Human Metabolism of the experimental cancer therapeutic agent d-limonene", Cancer Chemother. Pharmacol. (1994) 35: 31-37.
Crowell, "Prevention and Therapy of cancer by Dietary Monoterpenes," J. Nutrition (1999) 129(3): 775-778.
Dinkova-Kostova et al., Extremely potent triterpenoid induces of the Phase 2 response: Correlations of Protection . . . PNAS (2005) 102(12): 4584-4589.
Dragsted et al., "Cancer-protective factors in fruits and vegetables: biochemical and biological background", Pharmacology & Toxicology (1993) 1: 116-135.
Duarte et al., "New Macrocyclic Lathyrane Diterpenes, from *Euphorbia lagascae*, as Inhibitors . . . ", Planta Medica (2006) 72(2): 162-168.
Einbond et al., "Acetin and a Fraction of Black Cohosh Ptentiate Antiproliferative Effects of Chemotherapy" . . . Planta Medica (2006) 72(13): 1200-1206.
Einbond et al., "Gene Expression Analysis of the Mechanisms whereby Black Cohosh Inhibits . . . ", Anticancer Research (2007) 27(2): 697-712.
Gould, "Prevention and therapy of mammary cancer by monoterpenes", J. Cell. Biochem. (1995) 22: 139-144.
Gould, "Cancer Chemoprevention and Therapy by Monoterpenes", Environ. Health Perspectives (1997) 105: Suppl 977-979.
Katsuragi et al., "Characteristics of phosphadidic acril-containing lipoproteins which selectively inhibit bitter taste", Biochem Biophys Acta (1996) 1289: 322-328.

(Continued)

*Primary Examiner* — Suzanne Ziska
(74) *Attorney, Agent, or Firm* — Klauber & Jackson LLC (57) ABSTRACT

The present invention provides methods of treating humans and animals with terpenes and terpenoids in order to rejuvenate the skin and increase the protective layer against irradiation by ultraviolet radiation (UVR). More specifically it provides terpenes and terpenoids as ingredients that work as persistent UVR blockers. Terpenes and terpenoid compounds support the growth of skin, skin tissue and keratinocytes and additional UVR-blocking by reason of increased stratum corneum thickness and loricrin content. Both terpenes and terpenoids may be applied topically or orally at oral or topical concentrations from about 6 mg to about 600 mg per kilogram of body weight per day effective to stimulate growth of the skin layer and prevent damage from ultraviolet radiation (UVR).

13 Claims, 4 Drawing Sheets (56) References Cited

OTHER PUBLICATIONS

Kim et al., "Identification of a Novel Synthetic Triterpenoid, Methyl-2-cyano-3 . . . " Molecular Cancer Terapeutics (2002) 1(3): 177-184.
Lambert et al., "Inhibition of carcinogenesis by polyphenols; evidence from laboratory inventiations", Am. J. Clin. Nutr. (2005) 81(1): 284-291.
Lapczynski et al., "Fragrence material review on damascenone", Food and Chemical Toxicology (2007) 45(1): S172-S178.
Li et al., "Gene array of the hepatic response to endotoxin in glutathione peroxidose-deficient mice", Toxicology Letters (2003) 144(3): 397-406.
Liby et al., "The Synthetic Triterpenoids, CDDO and CDDO-Imidazolide are Potent Inducers of . . . " Cancer Research (2005) 65(11): 4789-4798.
Liby et al., "The Synthetic Triterpenoids CDDO-Methyl Ester and CDDO-Ethyl Amide . . . ", Cancer Research (2007) 67(6) 2414-2419.
Lluria-Prevatt et al.,"Effects of Perilyl Acohol on Melanoma in the T-Prase Mouse Model", Cancer Epidemiology, Biomarkers & Prevention (2002) 11(6): 573-579.
Lowe et al., "Systemic Retinoids in Psoriasis: Comparative Efficacy and Toxicity", Pharmacol Skin (1989) 3: 240-248.
Lu et al., "Different Gene Expression of Skin Tissues between Mice with Weight Controlled . . . ", Experimental Biology & Medicine (2007) 232(4): 473-480.
Morita et al., "Nonpeptide antigen, presentation mechaninsms and immunological memory of human . . . ", Immunological Reviews (2007) 215: 59-76.
Nakamura et al., Zesumbone, a tropical ginger sesquiterpene, activates Phase II drug metabolizing enzymes, FEBS Letters (2004) 572(1-3): 245-250.
Niwa et al., "Preventive effects of glycyshizin on estrogen-related endometrial cancinogenesis in mice", Oncology Reports (2007) 17(3): 617-622.
Pusztai et al., "Macrocyclic lathyrane diterpenes as antitumor promoters", Anticancer Research (2007) 27(1A): 201-205.
Rahman et al., "Gene Expression Profiling Revealed Surviving as a Target . . . ", Cancer Research (2006) 66(9): 4952-4960.
Ray, "Cancer preventive role of selected dietary factors", Indian J. Cancer (2005) 42(1): 15-24.
Rollman et al., "Psoriasis and Vitamin A Plazama Transport and Skin Content of Retinol . . . ", Arch Dermatol Res. (1985a) 278(1): 17-24.
Rollman et al., "Vitamin A in skin and serum studies of acne, vulgaris, atopic dermatitis . . . ", Br. J. Dermatol. (1985b) 113(4) 405-413.
Ruiz et al., "Detection of NaCl and KCI in TRPV1 Knockout Mice", Chemical Senses (2006) 31(9): 813-820.
Sengottuvelan et al., Chemopreventive effect of trans-reversatrol—a phytoolexyn against colonic . . . Carcinogenesis (2006) 27(5): 1038-1046.
Shishodia et al., "A synthetic triterpenoid, CDDO-Me, Inhibits IkappaBalpha Kinase and enhances . . . ", Clinical Canc. Res. (2006) 12(6): 1828-1838.
Steele et al., Mechanisms and applications of non-steroidal anti-inflammatory drugs . . . , Mutation Research (2003) 523-524: 137-144.
Verma et al., "Cytotoxicty of Oraganic Compounds against Ovarian Cancer Cells: A Quanitative Sructure . . . " Molec. Pharm. (2006) 3(4): 441-450.
Waladkhani et al., "Effects of dietary phytochemicals on cancer development", Int. J. Molec. Med. (1998) 1(4): 747-753.
Wei et al., "Reltionship of oxidative events and DNA oxidation in SENCAR mice to in vivo promoting . . . ", Carcinogenesis (1993) 14: 1195-1201.
Weinstein, "The Origins of Human Cancer: Molecular Mechanisms of Carcinogenesis and their . . . ", Cancer Research (1988) 48(15): 4135-4143.
Wu et al., "Dietary approach to atttenuate oxidative stress, hypertension and inflammation in the . . . ", PNAS (2004) 101(18): 7094-7099.
Ziegler et al., "Migration patterns and breast cancer risk in Asian-American women", Journal of the National Cancer Institute (1993) 85: 1819-1827.
Federal Register "Sunscreen Drug Products for over the counter Human use; Proprosed Amendement of final Monograph", (1978) 43(166): 38206-38269.
Gonzalez et al., "Polypodium Leucotomos Extract: A Nutraceutical with Photoprotective Properties", Drugs of Today (2007) 43: 00-00.
Gonzalez et al., "Mechanistic insights in the use of a *Polypodium leucotomos* extract as an oral and topical . . . ", Photochem Photobiol Sci (2010) 9: 559-563.
Plotto et al., "Odour and flavour thresholds for key aroma component in an orange juice matrix . . . ", Biochem J. (2004) 19: 491-498.
Powell et al.,"Bile acid hydrophobicity in correlation with inudction of apoptosis and/or growth arrest . . . ", Biochem J (2001) 356: 481-486.
Stahl et al., "Cartenoids and cartenois plus Vitamin E protect against ultriaviolet light-induced erythema in humans", Am J Clin Nutr (2000) 71: 795-798.
Svobodova et al., "Solar radiation induced skin damage: review of protective and preventive options" Int J Radiate Biol (2010) 86(12) 999-1030.
Thompson et al., "Dietary flaxseed alters tumor biological markers in postmenopausal breast cancer" Clin Cancer Res (2005) 11: 3828-3835.

\* cited by examiner

FIG. 2
Bar chart of level 4 categories under biological_process

METHODS OF BLOCKING ULTRAVIOLET RADIATION AND PROMOTING SKIN GROWTH USING TERPENES AND TERPENOIDS

CROSS REFERENCE TO RELATED APPLICATIONS

The present application claims the benefit under 35 U.S.C. §119(e) of U.S. provisional application 61/276,887, filed Sep. 17, 2009, the disclosure of which is herein incorporated by reference.

FIELD OF THE INVENTION

The present invention relates to methods of treating humans and animals with terpenes and terpenoids in order to rejuvenate the skin, stimulate the skin defense mechanism against ultraviolet radiation (UVR), and increase the skin protective layer against UVR. More specifically it relates to the use of terpenes and terpenoids, such as monoterpenoids, sesquiterpenes and norisoprenoids as ingredients that stimulate the skin defense mechanism against UVR.

BACKGROUND OF THE INVENTION

Terpenes and terpenoids represent a large complex class of compounds built upon the isoprene unit, $C_5H_8$. Some terpenes and terpenoids have been used in the food, flavor and fragrance industries. Typically they are of plant or microbial origin and are often bound to tannins or glycosides.

Terpenes, which are important contributors to many fruit and floral scents, are synthesized from geranyl diphosphate (GDP), an intermediate in carotenoid biosynthesis. Monoterpene perillyl alcohol has been reported to inhibit photocarcinogenesis in a non-melanoma model of mouse skin carcinogenesis and UVB-induced skin carcinogenesis. Perillyl alcohol caused a reduction in UVB-induced non-melanoma tumors (Barthelman et al., *Cancer Res.* 58:711-716, 1998). Topical pretreatment but not post-treatment of the melanoma cells with perillyl alcohol markedly reduced levels of UV-induced reactive oxygen species. These studies suggest that perillyl alcohol inhibits the Ras signaling pathway and thus can be an effective target for chemoprevention of melanoma (Lluria-Prevatt et al., *Cancer Epidemiology, Biomarkers & Prevention*, 11(6):573-579, 2002).

Numerous studies have shown major changes in gene expression patterns associated with terpene exposure (Nakamura et al., *FEBS Letters*, 572(1-3): 245-250, 2004; Einbond et al., *Anticancer Research*, 27(2):697-712, 2007; Rahman et al., *Cancer Research*, 66(9):4952-4960, 2006). Very frequently gene expression changes involve clusters of genes directly or indirectly involved in lowering rates of cell proliferation, increasing antioxidative enzymes and increasing apoptosis. Some terpenes can act directly on epithelial cells in vitro and produce many of the same responses seen in vivo (Kim et al., *Molecular Cancer Therapeutics*, 1(3):177-184, 2002). Some triterpenes exhibited cancer preventative capacity in breast, uterus, and lung cancer, respectively (Niwa et al., *Oncology Reports*, 17(3): 617-622, 2007; Liby et al., *Cancer Research*, 67(6): 2414-2419, 2007). Extract of a plant *Rabdosia rubescens* was reported to prevent cancer due to its content of diterpenoids (Ho et al., U.S. Pat. No. 7,351,739, 2008). Another plant extract from *Acacia victoriae* containing saponins suggested that it is the triterpenes which exhibited exhibit potent anti-tumor effects against a variety of tumor cells (Arntzen et al., US Patent Publication US2006/0073222 A1).

Kunsch et al., U.S. Pat. No. 7,247,714 suggests that certain compounds can activate cytoprotective response elements (CPREs) that have been identified to induce, coordinate and activate certain genes that protect cells from the potentially damaging effects of oxidative stress. CPREs have the DNA consensus sequence 5'-RTGACWNAGCANW-3', wherein R=A or G, W=A or T, and N=A, G, C or T. The cellular functions of CPRE regulated genes are diverse, however in general, these genes act in various capacities to regulate and maintain redox homeostasis in the cell. The CPRE is unique, and different from the antioxidant response element (ARE) and the maf-recognition element (MARE).

d-Limonene is a cyclic monoterpene that can serve as a precursor to a host of other oxygenated monocyclic monoterpenes such as carveol, carvone, menthol, perillyl alcohol and perillaldehyde. It is characterized as a non-nutritive dietary component. d-Limonene is found in the essential oils of citrus fruits, cherry, mint and herbs. It is widely used in foods, flavors, fragrances, house hold products and skin cleansing formulation. d-Limonene is metabolized to oxygenated metabolites in rats and in humans. In rats, the two major serum metabolites of d-limonene are perillic acid and dihydroperillic acid. d-Limonene and its metabolites are detectable in serum, liver, lung and many other tissues with higher concentrations detected in adipose tissue and mammary gland than in less fatty tissues (Crowell et al., *Cancer Chemother. Pharmacol.* 31:205-212, 1992). Humans produce these two serum metabolites as well as limonene-1,2-diol (Crowell et al., *Cancer Chemother. Pharmacol.* 35:31-37, 1994). Metabolism of perillyl alcohol and d-limonene are similar.

Nootkatone is a sesquiterpene, present in grapefruit, tangerine, orange juices and oils. It does not appear to be toxic, at least at the concentrations found in normal strength grapefruit juice (approximately 0.0035%, or 35 ppm).

Norisoprenoid beta-damascenone is a widely used fragrance and flavor material present in a wide variety vegetables and teas. It is found also in grapes and wine either glycosylated or as an aglycon. Between 1 and 10 metric tons are used annually in the flavor and fragrance industry. No phototoxicity or photoallergenity has been reported in humans after topical application of beta-damascenone and UV-radiation. No skin irritation was observed in mice, guinea pigs and humans up to 5%. Higher concentration than 5% has not been tested. The $LD_{50}$ was reported to be greater than 2.0 g/kg (Lapczynski et al., *Food and Chemical Toxicology*, 45(1): S172-S178, 2007).

Natural and synthetic vitamin A derivatives (retinoids) have been used extensively in the treatment of a variety of skin disorders and have been used as skin repair or renewal agents. Vitamin A is a diterpenoid. Compounds such as retinol occur naturally in the human body and are essential for normal epithelial cell differentiation. Retinoic acid, for example, has been used to treat a variety of skin conditions such as, for instance, acne, wrinkles, psoriasis, age spots and discoloration (Rollman and Vahlquist, *Arch Dermatol Res.*, 278(1):17-24, 1985a, and Rollman and Vahlquist, *Br J. Dermatol.*, 113(4): 405-413, 1985b; Lowe and David, *Pharmacol Skin* 3:240-248, 1989). Although retinoids efficiently arrest the cell cycle of many types of epithelial tumors during the $G_1$ stage, no single common mechanism of action has been identified. Retinal (preformed vitamin A) and/or certain carotenoids (provitamin A) are converted to retinol in the body, as needed. Retinol and the other retinoids are integrally involved in cell growth and differentiation, which may affect carcinogenesis.

Vitamin C (L-ascorbic acid) has been described for use in topical administration to reinforce the cohesion of the dermo-epidermal junction (Bernerd, F. U.S. patent application Ser. No. 10/358,888, 2003). Pharmacologically, ascorbate ion is an antioxidant which is required as cofactor in collagen synthesis. Some studies suggested that ingestion of vitamin C rejuvenates skin. The same was observed with omega-6-linolenic acid.

The epidermal cornified cell envelope is a complex protein-lipid composite that replaces the plasma membrane of terminally differentiated keratinocytes and is different than the stratum corneum, which is the external protective layer on the skin surface. The cornified envelope is a precursor structure for the corneum and has the ability to prevent the loss of water and ions and to protect from environmental hazards similar to that of the corneum. The major protein of the cornified cell envelope of the terminally differentiated keratinocytes is loricrin which is eventually crosslinked to the keratin of the corneum. Loricrin contributes about 70% to the protein mass of the envelope cells, but is a minor percentage of the protein mass of the corneum (Candi et al., *Nature Reviews Molecular Cell Biology* 6:328-340, 2005).

Its gene expression is limited to human keratinocytes of stratified squamous epithelia. A VEGF, or vascular endothelial growth factor, that represents in the skin a major angiogenesis factor, is downregulated after UV-light exposure. Matrix metalloproteinases (MMPs) are enzymes that degrade the extracellular matrix in the context of physiological remodeling of the skin, but age and exposure to UV radiation have the effect of increasing the activity of these MMPs, in particular that of MMP1, MMP3 and MIMP9.

UVR causes skin inflammation and redness (erythema) associated with sunburn. Sunscreen products typically applied in the form of a cream consist of active ingredients that adsorb UV-rays directly. Suitable sunscreens can have UVA absorbing properties, UVB absorbing properties or a mixture thereof. The exact amount of the sunscreen active may vary depending upon the desired Sun Protection Factor, i.e. the "SPF" of the composition as well as the desired level of UVA protection. SPF is a commonly used measure of photoprotection of a sunscreen against erythema. The SPF is defined as a ratio of the ultraviolet energy required to produce minimal erythema on protected skin to that required to produce the same minimal erythema on unprotected skin in the same individual (See, *Federal Register*, 43(166): 38206-38269, Aug. 25, 1978). Suitable sunscreens include, but are not limited to, those found in the CTFA International Cosmetic Ingredient Dictionary and Handbook, 7$^{th}$ edition, volume 2 pp. 1672, edited by Wenninger and McEwen (The Cosmetic, Toiletry, and Fragrance Association, Inc., Washington, D.C., 1997).

Suitable UVA absorbing sunscreen actives include, for instance, dibenzoylmethane derivatives, anthranilate derivatives such as methylanthranilate and homomethyl, 1-N-acetylanthranilate, and mixtures thereof. Examples of dibenzoylmethane sunscreen actives are described in U.S. Pat. No. 4,387,089 issued to Depolo; and in Sunscreens: Development, Evaluation, and Regulatory Aspects edited by N. J. Lowe and N. A. Shaath, Marcel Dekker, Inc (1990). These are all UVR absorbing type of sunscreen providing broad-spectrum UVA protection either independently, or in combination with, other UV protective actives that may be present in the composition.

Terpenes display some very interesting properties related to cancer prevention (Morita et al., *Immunological Reviews* 215: 59-76, 2007; Liby et al., *Cancer Research*, 67(6): 2414-2419, 2007; Niwa et al., *Oncology Reports*, 17(3): 617-622, 2007; Sengottuvelan et al., *Carcinogenesis*, 27(5): 1038-1046, 2006). Their relative safety makes them suitable for use in flavors and fragrances. Sometimes stereo-isomers of the same terpene have entirely different sensory profiles. Carvone is an example: 4R-(−)-carvone exhibits sweet spearmint flavor, whereas 4S-(+)-carvone tastes like caraway. Terpenes also tend to exhibit relatively high hydrophobicity and some are perceived as bitter to humans. Hydrophobicity allows terpenes to interact directly with cell membranes to trigger responses, such as greater level of anti-oxidation and apoptosis. Terpenes such as limonene, farnesol, geraniol and nerolidol have been suggested for transdermal and transmucosal drug delivery (e.g. Aqil et al., *Drug Discovery Today* 12(23-24):1061-1067, 2007). The penetration of terpenes is linked to their size, hydrophobicity, chirality, saturation and boiling point.

It seems that the receptor sites for bitter substances on the taste cells tends to be hydrophobic (Katsuragi et al., *Biochim Biophys Acta* 1289:322-328, 1996) and may provide a mechanism whereby terpenes can interact directly with cell membranes to trigger responses, such as greater levels of anti-oxidation and apoptosis. Two additional important characteristics of terpene flavors are intensity and threshold concentration which are determined by the specificity of receptors (Ruiz et al., *Chemical Senses* 31(9):813-820, 2006). Terpenes are useful as skin penetration enhancers and agents involved in the prevention and therapy of inflammatory diseases. Some terpenes are better at preventing cancer than others and some can extend lifespan in addition to preventing cancer. Activity generally tends to increase with the order of polyterpenes and also hydroxylation (Crowell et al., *Carcinogenesis* 13(7):1261-1264, 1992). Because of variable tastes and taste intensities and documented utility as dietary inhibitors of carcinogenesis, the huge variety of available terpenes provides a fertile field for establishing how they might be useful in sunburn protection and cancer prevention (Dragsted et al., *Pharmacology & Toxicology* 1:116-135, 1993; Craig, *American J. Clinical Nutrition* 70(3): 491-499, 1999; Ray, *Indian J. Cancer*, 42(1):15-24, 2005). Several terpenes have been established as cancer prevention agents in mice. Initiation of breast cancer induced by ionizing radiation or DMBA in rats was almost completely prevented by the monoterpene d-limonene and its hydroxylated derivative, perillyl alcohol, without any evidence of toxicity, and both agents were effective therapeutically as well (Crowell et al., Carcinogenesis 13(7): 1261-1264, 1992; Gould, *J. Cell. Biochem.* 22:139-144, 1995. Geraniol was about 5-fold more effective than perillyl alcohol against the growth of human transplanted pancreatic adenocarcinomas (Burke et al., *Lipids* 32(2):151-156, 1997).

A triterpene, actein, exhibited a synergistic therapeutic effect with 5-fluorouracil (a cancer chemotherapeutic agent) against human breast cancer cells in vitro apparently by causing increased apoptosis (Einbond et al., *Planta Medica* 72(13):1200-1206, 2006). The synthetic triterpene 2-cyano-3,12-dioxooleana-1,9(11)-dien-28-oic acid (CDDO) at nanomolar concentrations exhibited potent antiproliferative, pro-differentiation, and anti-inflammatory activities and large increases in the cytoprotective heme oxygenase-1 (HO-1) enzyme in vitro and in vivo. A similar inhibition of mouse lung tumors was noted based on anti-oxidative activity. (Liby et al., *Cancer Research* 65(11): 4789-4798, 2005; Liby et al., *Cancer Research* 67(6): 2414-2419, 2007). Mechanistic studies have found that triterpenes are strongly pro-apoptotic for human small cell lung cancer cells in vitro and act by blocking NF-KappaB thereby elevating apoptosis (Shishodia et al., *Clinical Canc. Res.* 12(6):1828-1838, 2006; Kim et al., *Molecular Cancer Therapeutics* 1(3): 177-184, 2002).

Numerous studies have shown major changes in gene expression patterns associated with terpene exposure (Nakamura et al., *FEBS Letters* 572(1-3): 245-250, 2004; Einbond et al., *Anticancer Research* 27(2):697-712, 2007; Gould, M. N. *Enciron. Health Perspectives* 105: Suppl, 977-979 1997; Rahman et al., *Cancer Research* 66(9): 4952-4960, 2006). Very frequently gene expression changes involve clusters of genes directly or indirectly involved in lowering rates of cell proliferation, increasing antioxidative enzymes and increasing apoptosis; all of which tend to block neoplastic growth. Several key genes that recur often in these studies are survivin, NFKappaB, TRAF, bcl-2 and IAP-2 (Shishodia et al., *Clin. Canc. Res.* 12(6):1828-1838, 2006). Colon cancer induced in rats by 1,2-dimethylhydrazine was inhibited 67% ($p<0.01$) by 8 mg/kg of the phytoalexin, resveratrol (Sengottuvelan et al., *Carcinogenesis* 27(5):1038-1046, 2006). Other studies show that hydrophobic receptors may play a role in causing apoptosis of cancer cells. Hydrophobic statins induced apoptosis and/or growth arrest in HCT116 cells (Powell et al., *Biochem. J.* 356:481-486, 2001) and the cytotoxicity of various organic compounds against ovarian cancer cells was correlated with their hydrophobic and steric properties (Verma et al., 3(4):441-450, 2006).

Hypotheses proposed to explain the cancer preventive activity of terpenes are generally variations on 1) altered cell signaling through gene expression changes, 2) antioxidative activity and 3) pro-apoptosis effects (Niwa et al., *Oncology Reports* 17(3):617-622, 2007; Shishodia et al., 12(6):1828-1838, 2006; Einbond et al., *Anticancer Research* 27(2):697-712, 2007; Pusztai et al., *Anticancer Research* 27(1A):201-205, 2007; Duarte et al., *Planta Medica* 72(2):162-168, 2006). Monoterpenes are known to inhibit the isoprenylation of small G proteins which affects signal transduction and alters gene expression and can affect the cell cycle (Gould, *Environ. Health Perpsectives* 105: 977-979, 1997). Studies of mammary cancer show a series of effects including blockage of the G1 phase of the cell cycle, followed by apoptosis, redifferentiation, and frequently complete tumor regression (Gould, *Environ. Health Perpsectives* 105: 977-979, 1997; Crowell, P. L. *J. Nutrition* 129(3):775-778, 1999). The theme that terpenes can activate apoptosis and can have antioxidative and anti inflammatory activity is recurrent in the literature (Ray, *Indian Journal of Cancer* 42(1):15-24, 2005; Wei et al., *Carcinogenesis* 14:1195-1201, 1993). For example, quercetin and omega-3-fatty acids in colorectal and prostate cancer responded to the terpene, lycopene (Lambert et al., *Am. J. Clin. Nutr.* 81(1):284-291, 2005. Others have found that the pyrophosphorylated isoprenoid intermediates and their metabolites are involved in the activation of the Vgamma2Vdelta2 T cells (Morita et al., *Immun. Reviews* 215:59-76, 2007), which enhances the removal of tumor cells because of better recognition by T-cells and natural killer receptors. Additionally, hydrophobicity and steric parameters of the terpenes may be one of the most important determinants of cytotoxic activity (Verma et al., *Molec. Pharm.* 3(4): 441-450, 2006). Some synthetic triterpenes are strong inhibitors of inflammatory processes like induction of nitric oxide synthase (iNOS) and COX2 but also elevate phase 2 responses, including heme oxygenase 2 via the Nrf2-Keap1 signaling pathway (Dinkova-Kostova et al., *PNAS* 102(12): 4584-4589, 2005).

SUMMARY OF THE INVENTION

In a first aspect, the present invention provides methods of decreasing the amount of UVR adsorbed by the living cells in the skin by administering a terpene or a terpenoid. This aspect of the invention may be alternatively described as a method of inhibiting UVR damage to the DNA of skin cells. In some embodiments, the terpene or terpenoid is administered orally or topically, in other embodiments, it may be administered parenterally.

The terpene or terpenoid may be administered 1, 2, 3, 4 or more hours prior to exposure to UVR, and it may be administered 1, 2, 3, 4, 5, 6, 7, or more days, 1 week, 2 weeks, a month, 2 months, 3 months, 6 months or more prior to exposure to UVR. Preferably, the terpene or terpenoid is administered within about 2 weeks of exposure to UVR. Likewise, the terpene or terpenoid may be administered 1, 2, 3, 4, 5, or 6 or more times per day. In some embodiments the composition contains one or more of terpenes or terpenoids. In a preferred embodiment, the terpenes or terpenoids utilized are administered in the amounts ranging from about 6 mg to about 600 mg per kilogram of body weight per day, more preferably ranging from about 60 mg to about 200 mg per kilogram of body weight per day. This dosage may be adjusted to provide the optimum prevention response. For example, several smaller doses may be taken daily. In some embodiments, the terpene or terpenoid is administered in an amount of approximately 0.001% (10 ppm) to 1% (10,000 ppm), and in some instances, the terpene or terpenoid is administered in the form of a solid or a liquid. In other instances, the terpene or terpenoid is administered orally or topically. The terpene or terpenoid may in some embodiments be administered orally or topically in an amount of about 1-1,000 μg, 1-500 μg, 1-250 μg, 1-100 μg, 1-50 μg, 1-25 μg, 5-50 μg, 10-40 μg, or 15-35 μg. In other embodiments, the terpene or terpenoid may be administered in droplets of about 1-1,000 μL, 1-500 μL, 1-250 μL, 1-100 μL, 1-50 μL, 1-25 μL, 5-50 μL, 10-40 μL, or 15-35 μL.

In preferred embodiments, the terpene or terpenoid is administered in a dosage and in amounts sufficient to reduce the amount of cutaneous inflammation and erythema present in the skin of subjects receiving the terpene or terpenoid compared to the amount of cutaneous inflammation and erythema present in the skin of subjects not receiving the terpene or terpenoid when both subjects or both sets of subjects are exposed to the same dosage of UVR. Similarly, the terpene or terpenoid may be administered in a dosage and in amounts sufficient to increase epidermal cell proliferation and increase keratin production in the skin of subjects receiving the terpene or terpenoid compared to the amount of epidermal cell proliferation and keratin production present in the skin of subjects not receiving the terpene or terpenoid when both subjects or both sets of subjects are exposed to the same dosage of UVR. Similarly, the terpene or terpenoid may be administered in a dosage or in amounts sufficient to promote wound healing or to increase the speed or amount of wound healing. Also, in preferred embodiments the terpene or terpenoid is administered in a dosage and in amounts sufficient to alter the production of certain gene products in the skin of subjects receiving the terpene or terpenoid compared to the amount of production of certain gene products present in the skin of subjects not receiving the terpene or terpenoid when both subjects or both sets of subjects are exposed to the same dosage of UVR. The gene products may be any one or more of, for instance, NFKappaB, COX1, COX2, MAPKS, PGE2, ODC, protein kinase C, INOS, PI3-AKT, TNF-A, AP1, NRF2, KEAP1 AND IKappa kinase. Also, in preferred embodiments the terpene or terpenoid is administered in a dosage and in amounts sufficient to increase the production of loricrin gene products in the skin of subjects receiving the terpene or terpenoid compared to the amount of production of loricrin gene products present in the skin of subjects not receiving the terpene or terpenoid when both subjects or both sets of subjects are exposed to the same dosage of UVR.

In a second aspect, the present invention provides methods of rejuvenating the skin by administering a terpene or a terpenoid. In some embodiments, the terpene or terpenoid is administered orally in other embodiments, it may be administered topically or parenterally.

The terpene or terpenoid may be administered 1, 2, 3, 4, 5, or 6 or more times per day. In some embodiments terpene is one or more of beta-damascenone, nootkatone, or limonene. In some embodiments, the terpene or terpenoid is administered in an amount of approximately 0.001% (10 ppm) to 1% (10,000 ppm), and in some instances, the terpene or terpenoid is administered in the form of a solid or a liquid. In other instances, the terpene or terpenoid is administered orally or topically. The terpene or terpenoid may in some embodiments be administered orally or topically in an amount of about 1-1,000 μg, 1-500 μg, 1-250 μg, 1-100 μg, 1-50 μg, 1-25 μg, 5-50 μg, 10-40 μg, or 15-35 μg. In other embodiments, the terpene or terpenoid may be administered in droplets of about 1-1,000 μL, 1-500 μL, 1-250 μL, 1-100 μL, 1-50 μL, 1-25 μL, 5-50 μL, 10-40 μL, or 15-35 μL. In a preferred embodiment, the terpenes or terpenoids utilized are administered in the amounts ranging from about 6 mg to about 600 mg per kilogram of body weight per day, more preferably ranging from about 60 mg to about 200 mg per kilogram of body weight per day. This dosage may be adjusted to provide the optimum prevention response. For example, several smaller doses may be taken daily.

In preferred embodiments, the terpene or terpenoid is administered in a dosage and in amounts sufficient to reduce the amount of cutaneous inflammation and erythema present in the skin of subjects receiving the terpene or terpenoid compared to the amount of cutaneous inflammation and erythema present in the skin of subjects not receiving the terpene or terpenoid when both subjects or both sets of subjects are exposed to the same dosage of UVR. Similarly, the terpene or terpenoid may be administered in a dosage and in amounts sufficient to increase epidermal cell proliferation and increase keratin production in the skin of subjects receiving the terpene or terpenoid compared to the amount of epidermal cell proliferation and keratin production present in the skin of subjects not receiving the terpene or terpenoid when both subjects or both sets of subjects are exposed to the same dosage of UVR. Similarly, the terpene or terpenoid may be administered in a dosage or in amounts sufficient to promote wound healing or to increase the speed or amount of wound healing. Also, in preferred embodiments the terpene or terpenoid is administered in a dosage and in amounts sufficient to alter the production of certain gene products in the skin of subjects receiving the terpene or terpenoid compared to the amount of production of certain gene products present in the skin of subjects not receiving the terpene or terpenoid when both subjects or both sets of subjects are exposed to the same dosage of UVR. The gene products may be any one or more of, for instance, NFKappaB, COX1, COX2, MAPKS, PGE2, ODC, protein kinase C, INOS, PI3-AKT, TNF-A, AP1, NRF2, KEAP1 AND IKappa kinase. Also, in preferred embodiments the terpene or terpenoid is administered in a dosage and in amounts sufficient to increase the production of loricrin gene products in the skin of subjects receiving the terpene or terpenoid compared to the amount of production of loricrin gene products present in the skin of subjects not receiving the terpene or terpenoid when both subjects or both sets of subjects are exposed to the same dosage of UVR.

In a third aspect, the present invention provides methods of promoting epidermal cell growth, such as keratinocyte growth, or methods of increasing keratin production by administering a terpene or a terpenoid. In some embodiments, the terpene or terpenoid is administered orally or topically in other embodiments, it may be administered parenterally.

The terpene or terpenoid may be administered 1, 2, 3, 4, 5, or 6 or more times per day. In some embodiments terpene is one or more of beta-damascenone, nootkatone, or limonene. In a preferred embodiment, the terpenes utilized are administered in the amounts ranging from about 6 mg to about 600 mg per kilogram of body weight per day, more preferably ranging from about 60 mg to about 200 mg per kilogram of body weight per day. This dosage may be adjusted to provide the optimum prevention response. For example, several smaller doses may be taken daily. In some embodiments, the terpene or terpenoid is administered in an amount of approximately 0.001% (10 ppm) to 1% (10,000 ppm), and in some instances, the terpene or terpenoid is administered in the form of a solid or a liquid. In other instances, the terpene or terpenoid is administered orally. The terpene or terpenoid may in some embodiments be administered orally in an amount of about 1-1,000 μg, 1-500 μg, 1-250 μg, 1-100 μg, 1-50 μg, 1-25 μg, 5-50 μg, 10-40 μg, or 15-35 μg. In other embodiments, the terpene or terpenoid may be administered in droplets of about 1-1,000 μL, 1-500 μL, 1-250 μL, 1-100 μL, 1-50 μL, 1-25 μL, 5-50 μL, 10-40 μL, or 15-35 μL.

In preferred embodiments, the terpene or terpenoid is administered in a dosage and in amounts sufficient to reduce the amount of cutaneous inflammation and erythema present in the skin of subjects receiving the terpene or terpenoid compared to the amount of cutaneous inflammation and erythema present in the skin of subjects not receiving the terpene or terpenoid when both subjects or both sets of subjects are exposed to the same dosage of UVR. Similarly, the terpene or terpenoid may be administered in a dosage and in amounts sufficient to increase epidermal cell proliferation and increase keratin production in the skin of subjects receiving the terpene or terpenoid compared to the amount of epidermal cell proliferation and keratin production present in the skin of subjects not receiving the terpene or terpenoid when both subjects or both sets of subjects are exposed to the same dosage of UVR. Similarly, the terpene or terpenoid may be administered in a dosage or in amounts sufficient to promote wound healing or to increase the speed or amount of wound healing. Also, in preferred embodiments the terpene or terpenoid is administered in a dosage and in amounts sufficient to alter the production of certain gene products in the skin of subjects receiving the terpene or terpenoid compared to the amount of production of certain gene products present in the skin of subjects not receiving the terpene or terpenoid when both subjects or both sets of subjects are exposed to the same dosage of UVR. The gene products may be any one or more of, for instance, NFKappaB, COX1, COX2, MAPKS, PGE2, ODC, protein kinase C, INOS, PI3-AKT, TNF-A, AP1, NRF2, KEAP1 AND IKappa kinase. Also, in preferred embodiments the terpene or terpenoid is administered in a dosage and in amounts sufficient to increase the production of loricrin gene products in the skin of subjects receiving the terpene or terpenoid compared to the amount of production of loricrin gene products present in the skin of subjects not receiving the terpene or terpenoid when both subjects or both sets of subjects are exposed to the same dosage of UVR.

In a fourth aspect, the present invention provides methods of promoting wound healing, or methods of increasing the speed or amount of wound healing by administering a terpene or a terpenoid. In some embodiments, the terpene or terpenoid is administered orally or topically in other embodiments, it may be administered parenterally.

The terpene or terpenoid may be administered 1, 2, 3, 4, 5, or 6 or more times per day. In some embodiments terpene is one or more of beta-damascenone, nootkatone, or d-limonene. In a preferred embodiment, the terpenes utilized are administered in the amounts ranging from about 6 mg to about 600 mg per kilogram of body weight per day, more preferably ranging from about 60 mg to about 200 mg per kilogram of body weight per day. This dosage may be adjusted to provide the optimum prevention response. For example, several smaller doses may be taken daily. In some embodiments, the terpene or terpenoid is administered in an amount of approximately 0.001% (10 ppm) to 1% (10,000 ppm), and in some instances, the terpene or terpenoid is administered in the form of a solid or a liquid. In other instances, the terpene or terpenoid is administered orally. The terpene or terpenoid may in some embodiments be administered orally in an amount of about 1-1,000 µg, 1-500 µg, 1-250 µg, 1-100 µg, 1-50 µg, 1-25 µg, 5-50 µg, 10-40 µg, or 15-35 µg. In other embodiments, the terpene or terpenoid may be administered in droplets of about 1-1,000 µL, 1-500 µL, 1-250 µL, 1-100 µL, 1-50 µL, 1-25 µL, 5-50 µL, 10-40 µL, or 15-35 µL.

In preferred embodiments, the terpene or terpenoid is administered in a dosage and in amounts sufficient to reduce the amount of cutaneous inflammation and erythema present in the skin of subjects receiving the terpene or terpenoid compared to the amount of cutaneous inflammation and erythema present in the skin of subjects not receiving the terpene or terpenoid when both subjects or both sets of subjects are exposed to the same dosage of UVR. Similarly, the terpene or terpenoid may be administered in a dosage and in amounts sufficient to increase epidermal cell proliferation and increase keratin production in the skin of subjects receiving the terpene or terpenoid compared to the amount of epidermal cell proliferation and keratin production present in the skin of subjects not receiving the terpene or terpenoid when both subjects or both sets of subjects are exposed to the same dosage of UVR. Similarly, the terpene or terpenoid may be administered in a dosage or in amounts sufficient to promote wound healing or to increase the speed or amount of wound healing. Also, in preferred embodiments the terpene or terpenoid is administered in a dosage and in amounts sufficient to alter the production of certain gene products in the skin of subjects receiving the terpene or terpenoid compared to the amount of production of certain gene products present in the skin of subjects not receiving the terpene or terpenoid when both subjects or both sets of subjects are exposed to the same dosage of UVR. The gene products may be any one or more of, for instance, NFKappaB, COX1, COX2, MAPKS, PGE2, ODC, protein kinase C, INOS, PI3-AKT, TNF-A, AP1, NRF2, KEAP1 AND IKappa kinase. Also, in preferred embodiments the terpene or terpenoid is administered in a dosage and in amounts sufficient to increase the production of loricrin gene products in the skin of subjects receiving the terpene or terpenoid compared to the amount of production of loricrin gene products present in the skin of subjects not receiving the terpene or terpenoid when both subjects or both sets of subjects are exposed to the same dosage of UVR.

In a fifth aspect, the present invention provides compositions useful for one or more of increasing the amount of UVR that the skin can block or absorb, for inhibiting UVR damage to the skin, for rejuvenating the skin, for promoting epidermal cell growth, such as keratinocyte growth, or increasing keratin production, or for promoting wound healing, or increasing the speed or amount of wound healing containing one or more terpene or terpenoid. In a preferred embodiment, the terpenes are provided in amounts sufficient to be administered in amounts ranging from about 6 mg to about 600 mg per kilogram of body weight per day, more preferably ranging from about 60 mg to about 200 mg per kilogram of body weight per day. This dosage may be adjusted to provide the optimum prevention response. For example, several smaller doses may be taken daily. The terpene or terpenoid may in some embodiments be provided in an amount of about 1-1,000 µg, 1-500 µg, 1-250 µg, 1-100 µg, 1-50 µg, 1-25 µg, 5-50 µg, 10-40 µg, or 15-35 µg. In other embodiments, the terpene or terpenoid may be provided in a droplet in an amount of about 1-1,000 µL, 1-500 µL, 1-250 µL, 1-100 µL, 1-50 µL, 1-25 µL, 5-50 µL, 10-40 µL, or 15-35 µL. The composition containing the terpene or terpenoid may further contain other ingredients, such as, for instance a pharmaceutically acceptable carrier. The composition may be a liquid or a solid, such as for instance a tablet, lozenge or pill, and may be administered orally, topically or parenterally.

In a sixth aspect, the present invention provides a kit containing one or more compositions useful for one or more of increasing the amount of UVR that the skin can block or absorb, for inhibiting UVR damage to the skin, for rejuvenating the skin, for promoting epidermal cell growth, such as keratinocyte growth, or increasing keratin production, or for promoting wound healing, or increasing the speed or amount of wound healing. The compositions contain one or more terpene or terpenoid. In a preferred embodiment, the terpenes are provided in amounts sufficient to be administered in the amounts ranging from about 6 mg to about 600 mg per kilogram of body weight per day, more preferably ranging from about 60 mg to about 200 mg per kilogram of body weight per day. This dosage may be adjusted to provide the optimum prevention response. For example, several smaller doses may be taken daily. The terpene or terpenoid may in some embodiments be provided in an amount of about 1-1,000 µg, 1-500 µg, 1-250 µg, 1-100 µg, 1-50 µg, 1-25 µg, 5-50 µg, 10-40 µg, or 15-35 µg. In other embodiments, the terpene or terpenoid may be provided in a droplet in an amount of about 1-1,000 µL, 1-500 µL, 1-250 µL, 1-100 µL, 1-50 µL, 1-25 µL, 5-50 µL, 10-40 µL, or 15-35 µL. The composition containing the terpene or terpenoid may further contain other ingredients, such as, for instance a pharmaceutically acceptable carrier. The composition may be a liquid or a solid, such as for instance a tablet, lozenge or pill, and may be administered orally, topically or parenterally. The kit further contains instructions for administering, providing or taking the composition.

BRIEF DESCRIPTION OF THE FIGURES

FIG. 3 demonstrates a protective effect of ingested terpenes against the sunburn effect of solar-spectrum UVR in the skin of SKH1 hairless mice (FIG. 3A) and shows that the terpenes stimulate epidermal hyperplasia and increase the thickness of the keratin layer (FIG. 3B). The cutaneous inflammation and erythema associated with a 15 minute exposure of hairless mouse skin to 3.0 kJ/m2 of UVR was blocked in mice that were fed 4 daily 30 microL droplets of 3 different terpenes (d-limonene, nootkatone and beta-damascenone) per os.

DETAILED DESCRIPTION OF THE PREFERRED EMBODIMENTS

The present invention is based in part upon results from experiments using animal models demonstrating that ingestion of terpenes such as beta-damascenone, d-limonene and nootkatone results in UVR-protection, increased keratinocyte formation, upregulation of loricrin and vascular endothelial growth factor (VEGF) genes, and downregulation of matrix metalloproteinases. The present invention is based in part upon the discovery that terpenes and terpenoids promote UVR-absorbing hyperplasia and/or hyper keratinization. The terms "terpene" and "terpenoid" are defined very broadly herein. The terms "terpene" and "terpenoid" are meant to include all compounds that comprise hydrocarbons containing one or more of an isoprene unit [$CH_2=C(CH_3)-CH=CH_2$ or $(C_5H_8)_n$]. The terpenoid may be one of the acyclic terpenoids, cyclic terpenoids, cycloaliphatic compounds that are structurally related to terpenoids, and mixtures thereof. The terpenoids include terpenes and terpene derivatives such as, for instance, alcohols, aldehydes, acetals, ketones, acids, esters, and terpene compounds that contain heteroatoms such as nitrogen or sulfur, and mixtures thereof. Further, the terpenoids include such compounds as Myrcene, Ocimene, beta-FrameSene, Dihydromyrcenol, Geraniol, Nerol, Linalool, Myrcenol, Lavandulol, Citronellol, Trans-trans-Farnesol, Trans-Nerolidol, Citral, Citral diethyl acetal, Citronellal, Citronellyloxyacetaldehyde, 2,6,10-Trimethyl-9-undecenal, Tagetone, Solanone, Geranylacetone, Cis-Geranic acid Citronellic acid, Geranyl formate, Geranyl acetate, Geranyl propionate, Geranyl isobutyrate, Geranyl isovalerate, Neryl acetate, Lynalyl formate, Linalyl acetate, Linalyl propionate, Linalyl butyrate, Linalyl isobutyrate, Lavendulyl acetate, Citronellyl formate, Citronellyl acetate, Citronellyl propionate, Citronellyl isobutyrate, Citronellyl isovalerate, Citronellyl tiglate, Cis-Geranic acid nitrile, Citronellic acid nitrile, and mixtures thereof. Still further, the terpenoid may be one of Limonene, Alpha-Terpinene, Gamma-Terpinene, Terpinolene, Alpha-Phellandrene, Beta-Phellandrene, Alpha-Pinene, Beta-Pinene, Camphene, 3-Carene, Caryophytlene, (+)-Valencene, Thujopsene, Alpha-Cedrene, Beta-Cedrene, Longifolene, (+)-Neoiso-isopulegol, Isopulegol, Alpha-Terpineol, Beta-Terpineol, Gamma-Terpineol, Delta-Terpineol, 1-Terpinen-4-ol, Carvone, Alpha-Ionone, Beta-Ionone, Gamma-Ionone, Alpha-hone, beta-hone, gamma-bone, alpha-n-Methylionone, beta-n-Methylionone, gamma-n-Methylionone, alpha-Isomethylionone, beta-Isomethylionone, gamma-Isomethylionone, Allylionone, Pseudojonone, n-Methylpseudoionone, Isomethylpseudoionone, Damascones, beta-Damascenone, Nootkatone, Cedryl methyl ketone, Alpha-Terpinyl acetate, Nopyl acetate, Khusymil acetate, and mixtures thereof. In addition, the terpenoid may be a cycloaliphatic compound structurally related to terpenoids such as 5-(2,2,3-Trimethyl-3-cyclopenten-1-yl)-3-methylpentan-2-ol, 2,4-Dimethyl-3-cyclohexene carboxaldehyde, 4-(4-Methyl-3-penten-1-yl)-3-cyclohexene carboxaldehyde, 4-(4-Hydroxy-4-methypentyl)-3-cyclohexene carboxaldehyde, Civetone, Dihydrojasmone, Cis-Jasmone, 5-Cyclohexadecen-1-one, 2,3,8,8-Tetramethyl-1,2,3,4,5,6,7,8-octahydro-2-napthalenyl methyl ketone, 3-methyl-2-cyclopenten-2-ol-1-one, 4,7-Methano-3a,4,5,6,7,7a-hexahydro-5-(or 6)-indenyl acetate, Allyl 3-cyclohexylpropionate, Methyl dihydrojasmonate methyl (3-oxo-2-pentylcyclopentyl)acetate, and mixtures thereof.

These data demonstrate that terpenes and terpenoids provide a protective effect against UVR damage to the skin of hairless mice. The skin inflammation associated with exposure of hairless mouse skin to UVR was blocked in mice that were fed 3 different terpenes (d-limonene, nootkatone and beta-damascenone). On the contrary, daily exposures to terpenes following UVR exposure failed to produce any protective effect, indicating that anti-oxidation is not a likely explanation of the protective effect when the terpenes precede the UVR exposure. Histopathology results demonstrate well that terpenes trigger hyperplasia of the skin. Terpenes and terpenoids provide a three to five-fold increase in keratinocytes demonstrating that the terpenes alter the skin response prior to exposure to the UVR.

Terpenes may suppress cancer induction by activating genes that produce UVR-absorbent keratin thereby reducing photodamage to DNA or by inactivating inflammation-relevant genes that otherwise would elevate oxidative DNA damage. Diet is proven to exert major influences on cancer incidence in human populations (Lu et al. *Experimental Biology & Medicine* 232(4): 473-480, 2007; Wu et al. *PNAS* 101(18):7094-7099, 2004; Borek, C. *Integrative Canc. Therapies* 3(4):333-341, (2004); Li et al., *Toxicology Letters* 144(3):397-406, 2003). Migrants often acquire the cancer risks of their adopted land much more quickly than could be expected based on any known natural selection process (Ziegler et al., *Journal of the National Cancer Institute* 85: 1819-1827, 1993). In lab animals, work is currently focused on elucidating the underlying mechanisms of cancer chemoprevention for a variety of preventive compounds (Weinstein, *Cancer Research,* 48(15):4135-4143, 1988; Dragsted et al., *Pharmacology & Toxicology* 72: 116-135, 1993; Steele et al., *Mutation Research* 523-524:137-144, 2003; Waladkhani et al., *Int. J. Molec. Med.* 1(4):747-753, 1998). Terpenes are a family of compounds commonly found in the vital juices of plants. They include some of the most potent chemopreventive agents known, e.g. lycopene and perillyl alcohol, and generally have been proven safe as dietary additives. The possibility cannot be discounted that a portion of the anticarcinogenic effect of vegetable-based diets is based on the terpene content.

Two separate types of DNA damage, direct and oxidative, in epithelial cell DNA following the same exposure protocols for UVR and terpenes have been quantified. Cyclobutyl pyrimidine dimers (CPDs) and 8-oxo-dG are often utilized as a measure of direct UVR-induced DNA damage and oxidative DNA damage respectively. It may be that terpene-induced UVR absorption is the basis for sunburn and cancer preventive activity of the terpenes.

An important clue to the mechanism of the terpene effect was obtained from histological evaluation of skin samples from the preliminary experiment. Terpenes stimulated epidermal cell proliferation and keratin production. The combination of a thicker epidermis and keratin layer may have acted as a shield by absorbing some portion of the UVR. Such a possibility was reinforced by the observation that the increased epidermal thickness (hyperplasia) was more pronounced in the mice that received both, terpene and UVR, which raises the possibility that the response may be a protective adaptation to UVR. A literature search turned up nothing related to proliferative stimulation of epithelial cells by terpenes in skin or any other organ. Some reports show an opposite effect, i.e. terpenes block proliferation and induce apoptosis in several organs, but there were no reports of such activity in skin. Histopathological diagnosis was performed on the skin samples. Histopathology results demonstrated remarkably well, that the terpenes triggered the hyperplasia of the epidermis. Three to five-fold additional increases in keratinocyte layers demonstrates that the terpenes alter the skin response to the UVR. One can speculate that either a metabolic product or the terpenes themselves could trigger the increased proliferation of the epidermal basal cells.

The significance of these preliminary findings is that terpenes could be initiating a new type of sunblock, the mechanism of which is currently unknown but could be part of an adaptation that is analogous to the well-known UVR-blocking effect of melanin.

By "effective amount" is meant such amount that is capable of performing the function of the compound or property for which an effective amount is expressed. As known to those skilled in art, the exact amount required may vary from case to case, depending on recognized variables such as, for example, the compounds employed and the individual subject treated. Thus, it is often not desirable to specify an exact "effective amount." However, an appropriate effective amount may be determined by one of ordinary skill in the art using only routine experimentation.

It will be apparent to those skilled in the art that it is not intended that the invention be limited by the examples, and that the modifications can be made without departing from the invention, as defined by the appended claims. It is intended that all modifications and variations be included with the scope of the invention. The claims are meant to cover the claimed components and steps in any sequence that is effective to meet the objectives there intended, unless the context specifically indicates the contrary.

EXAMPLE 1

A pharmaceutical or dietary supplement form may be made by conventional procedures known in the industry that is by mixing active compounds with edible acceptable solid or liquid carriers or excipients in any form capsules, tablets, dragees, saches, films, powders, lozenges, syrups, liquid suspensions, emulsions and solutions in a convenient dosage form. Three different formulations of terpenes were made for oral usage and two formulations for topical application. Effective amount of terpene is needed to provide protection against UVR. Generally, an effective amount of the oral formulation is taken per day for the duration of 1-7 days prior to the UVR, or more preferably 3-4 days, in association with a carrier, and particularly one in which the active ingredients are soluble per se or are effectively solubilized (e.g. as an emulsion or microemulsion). The terpenes may be administered in the amounts ranging from about 6 mg to about 600 mg per kilogram of body weight per day, more preferably ranging from about 60 mg to about 200 mg per kilogram of body weight per day. This dosage may be adjusted to provide the optimum prevention response. For example, several smaller doses may be taken daily.

| Formulation I | |
| --- | --- |
| Terpene | 50% by weight (0.4 g/capsule) |
| Sunflower oil | 50% by weight (0.4 g/capsule) |

Capsules are prepared by dispersing active ingredient terpene in the liponate oil or any other oil such as sunflower, canola, etc. oils. The oil can be used as is or can be filled into soft, elastic gelatin capsules.

| Formulation II | |
| --- | --- |
| Terpene | 50% by weight (0.4 g/tablet or capsule) |
| Microcrystalline cellulose | 25% by weight (0.2 g/tablet or capsule) |
| Lactose BP | 25% by weight (0.2 g/tablet or capsule) |
| Ethyl cellulose | 0.1 g for coating of a tablet |

Terpenes, microcrystalline cellulose, and lactose BP are mixed, and extruded which is followed by spheronisation of the extrudate and drying. The dried pellets are then coated with release-controlling membrane (ethyl cellulose) and filled into a two-piece, hard gelatin capsule.

According to the invention, the formulations are administered topically (transdermally) when terpenes are applied in various carriers such as lubricants, wetting agents, emulsifying and suspending agents, preservatives, antiirritants, emulsion stabilizers, film formers, gel formers, odor masking agents, resins, hydrocolloids, solvents, solubilizers, neutralizing agents, permeation accelerators, pigments, quaternary ammonium compounds, refatting and superfatting agents, ointments, cream or oil base materials, silicone derivatives, stabilizers, sterilizing agents, propellants, drying agents, opacifiers, thickeners, waxes, emollients, or white oils. Suitable carriers can be water, alcohols, oils which can dissolve or disperse active ingredient. It is contemplated that in addition to the active ingredient terpene one or more antioxidants are also used.

The active ingredient may be administered preferably once a day for the duration of 1-7 days, more preferably between 3-4 days prior to the UVR. An effective amount of terpene is needed to provide protection against UVR. Generally, an effective amount of the topical formulation is applied to exposed skin sites in association with a carrier, and particularly one in which the active ingredients are soluble per se or are effectively solubilized (e.g. as an emulsion or microemulsion). Preferably, the formulation contains 0.05 to 50% by weight of terpene. Desirably, it will contain 0.1%-20% by weight, or more preferably 0.2-5% by weight of terpene.

| Formulation III | |
| --- | --- |
| Terpene | 1% by weight (1 g) |
| Liponeate oil | 99% by weight (99 g) |

The terpene component is mixed with the oil part, mixed well together to ensure complete solution. The mixture is used topically as such for 3-4 days prior to the UV radiation.

| Formulation IV | |
| --- | --- |
| Terpene | 1% by weight (1 g) |
| Creme base | 99% by weight (99 g) |

The active ingredient terpene is mixed with other components of the crème together to ensure complete distribution of terpene. The mixture is applied topically as such for 3-4 days prior to the UVR.

Experimental Design
1. experiment with various concentrations
2. experiment with delayed exposure
3. experiment with topical application, 100%
4. experiment with various topical concentrations All experiments were performed with female hairless mice (SKH1) utilizing solar spectrum ultraviolet radiation (UVR). Each experiment was performed in triplicate including controls and UVR-exposed mice and included a total of 22 mice per experiment for a total of 66 mice. The protocol included untreated mice, UVR-irradiated mice as controls for the terpene treatments, UVR+terpene mice and terpene-only mice.

Four solar simulating FS-20 fluorescent lamps were used to deliver 3 kJ/m² measured by a calibrated International Light UV radiometer at the lamp distance between 20 to 24 cm. The UVR dose was selected to be just above the minimal erythemal dose for producing a 'sunburn' reaction in mouse skin (this is very similar to the minimal erythemal dose of fair-skinned humans).

Three terpenes, d-limonene, nootkatone and beta-damascenone, were tested for their sunburn prevention potency. Each terpene was given to each mouse per os (by mouth) in 15-30 µL droplets (~15-30 µg) via micropipette once each day for 4 consecutive days prior to and/or subsequent to UVR exposure. Animals were observed and photographed every 24 hours for a period of 6-7 days after the irradiation. Each terpene was administered in pure form. Terpene d-limonene was also tested for its sunburn prevention potency when UVR delivered with a delay. Pure d-limonene was given to mice per os in the amount of 20 µA per day for four (4) days. The UVR exposure of 3 kJ/m² was delivered seven (7) days after the last dose was administered. The animals were observed and photographed. No erythema was observed. Terpene d-limonene was also tested topically to prevent sunburn. Pure or diluted d-limonene, 20 µl was spread on the dorsal part of mice for four (4) days prior to the UVR exposure of 3 kJ/m². Liponeate, a triglyceride fraction of coconut oil was used as a diluent. Concentration 1, 10 and 100% were tested. Development of erythema was observed and photographed after 6-7 days.

Synergy of terpenes was tested by applying a mixture of three different terpenes that were mixed in equal proportion. The mixture (20 µl) was applied on the dorsal part of mice for four (4) days prior to the UVR exposure of 3 kJ/m2. Development of erythema was observed and photographed after 6-7 days. The efficacy of the mixture was compared against individual terpenes at the same concentration.

All three terpenes exhibited complete sunburn protection when given prior to the UVR, but were inactive given after the UVR. The histology showed that the terpenes stimulated epidermal hyperplasia (piling up indicating proliferation).

Animals for the histology and microarray analysis were euthanized 24 hours after 4 days of terpene pre-feed and the UVR exposure. Tissue samples from skin and other organs were frozen and prepared for histological diagnosis and for microarray analysis, which consisted of testing gene expression by utilizing Affymetrix mouse microarray chips containing about 39,000 transcripts with 45,101 probe sets. Individual genes found to be induced by the UVR were predominantly inflammation-related and included NFKappaB, COX1, COX2, MAPKs, PGE2, ODC, protein kinase C, iNOS, PI3-Akt, TNF, AP1, Nrf2, Keap1 and IKappa kinase. Significant reductions in the constellation of inflammation-related genes was noted in the mice exposed to the terpenes, which is consistent with the protective action of the terpenes against sunburn, which is basically an inflammatory reaction to the UVR exposure.

Gene expression microarray analysis was performed as follows: RNA was extracted from a 0.1 g sample of mouse skin and an equal quantity of keratinocytes by using the TRIZOL reagent (Invitrogen, Carlsbad, Calif., USA) according to the manufacture's instructions and 200 µg of total RNA was used for the isolation of poly A+ mRNA by using Oligotex mRNA mini columns (QIAGEN, Valencia, Calif., USA). The final centrifugation was performed after the incubation with 1/10 volume of 3.0 M NaOAc, 2.5 volumes of ethanol and 1 µl glycogen (Boehringer Mannheim GmbH, Mannheim, Germany) at −20° C. overnight. Then the pellet was resuspended in diethylpyrocarbonate (DEPC)-treated water. RNA was labeled with biotin and hybridized to a Mouse genome 430_2 GeneChip® microarray (Affymetrix, Inc. Santa Clara, Calif., USA). Data from the Affymetrix mouse expression array chip were imported into the BRB-Array-Tools Version 3.3.0 developed by the Biometric Research Branch of the U.S. National Cancer Institute for normalization and analysis. Statistical comparison between the treated group and control group based on three replicates was performed by using the class comparison tool of BRB Array Tool software, which uses two sample T-tests (with random variance model) to find genes whose expression varied significantly. A value of $P \leq 0.001$ was chosen as statistically significant. In order to identify significantly altered categories of genes, the Gene Ontogeny website was utilized as documented in the GOTree Machine software suite. A list of significantly altered genes derived from the BRB-ArrayTools software was uploaded into the GOTree software for derivation of significantly altered gene categories. For these calculations the entire list of genes on the Affymetrix (mouse 430_2) microarray was used as the reference list.

Figure 1:
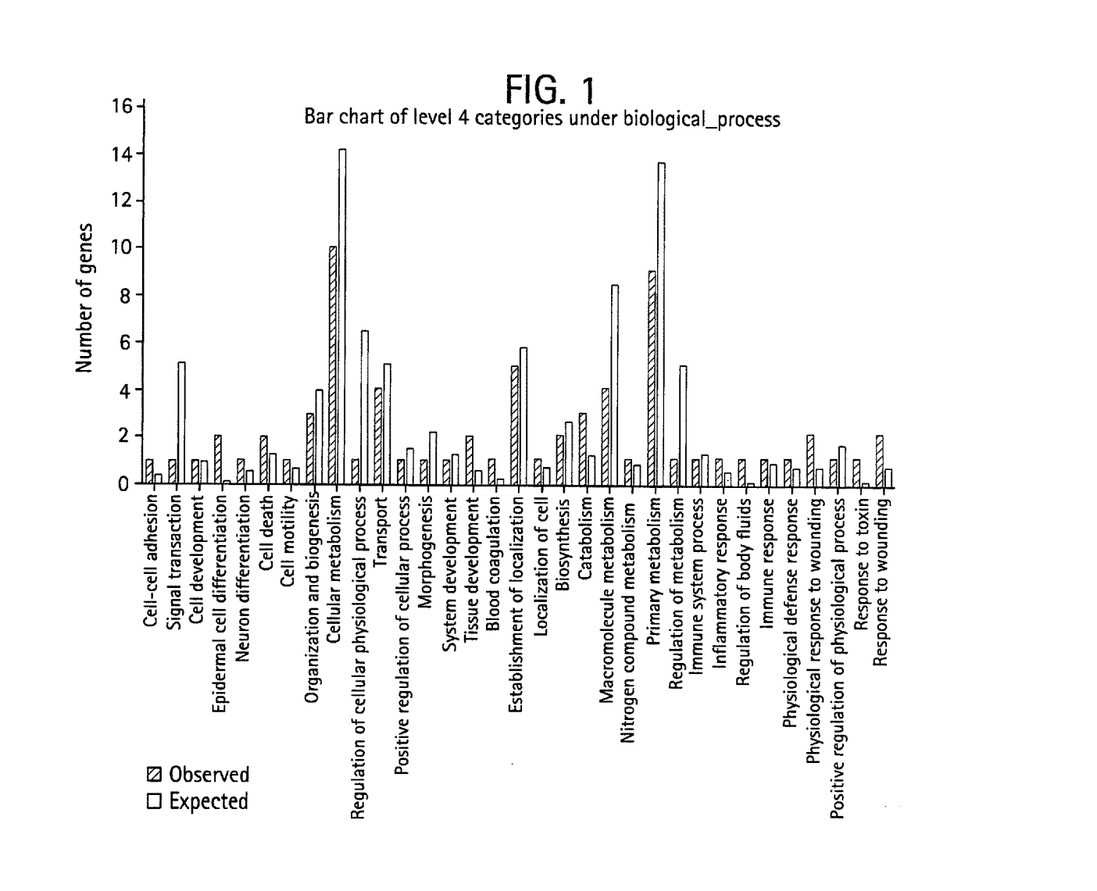
FIG. 1 shows 253 2-fold upregulated genes sorted into categories. Only the category of epidermal cell differentiation (red color) was significantly altered in comparison to random. The loricrin gene was included in this category.
Figure 2:
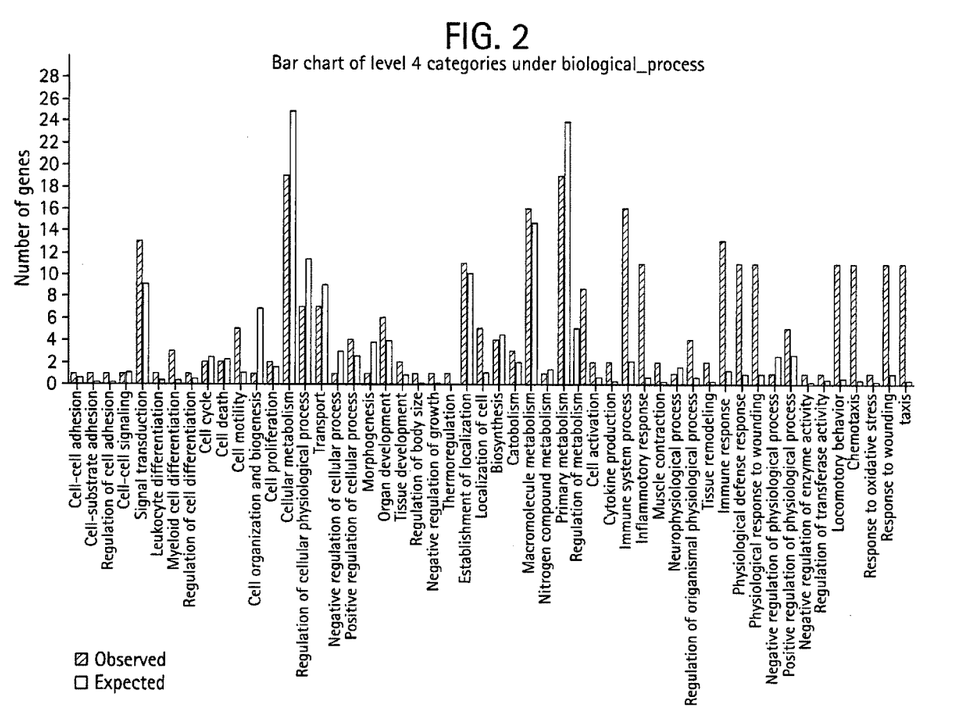
FIG. 2 shows 341 2-fold down-regulated genes sorted into gene categories. The significantly altered categories in comparison to random are shown in red and include many stress-response type of categories.
Figure 3A:
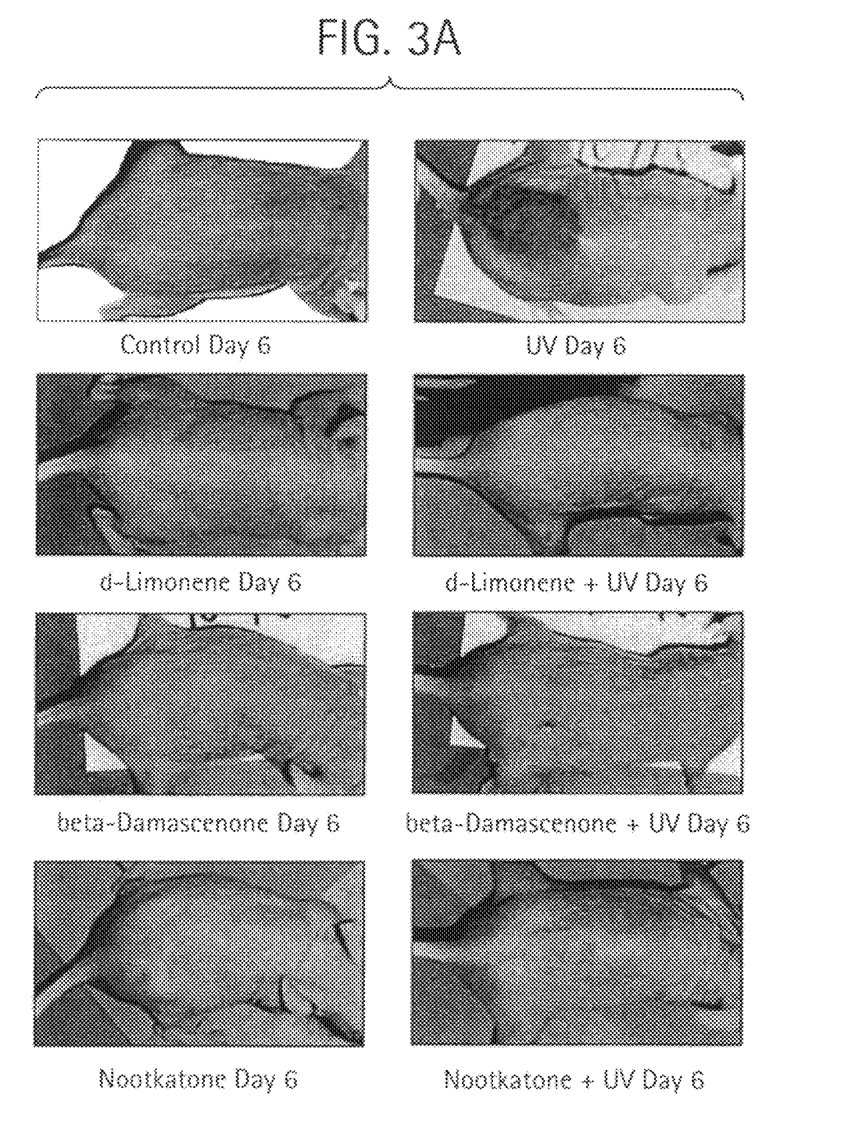
Figure 3B:
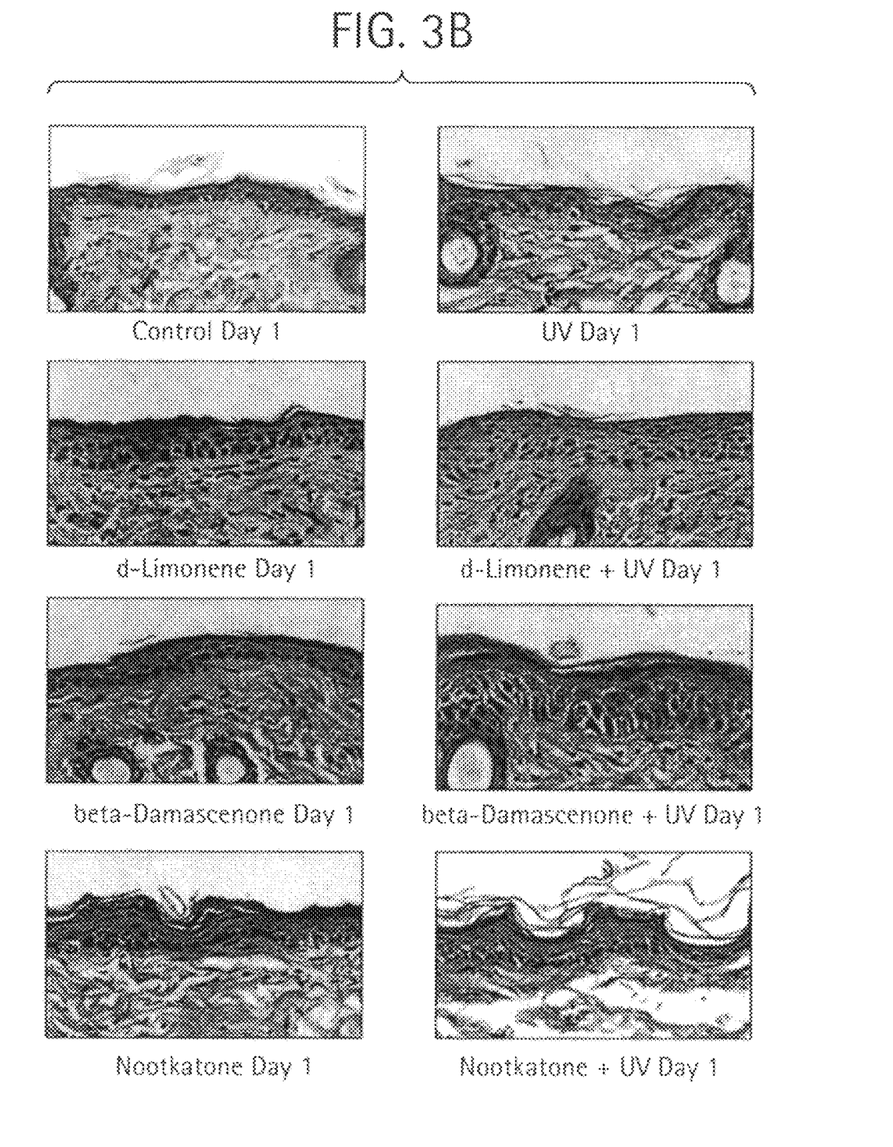

Mice were treated with either UVR or UVR+beta-damascenone, and samples of tissue were removed from the dorsal skin for RNA extraction and analysis on an Affymetrix Microarray System utilizing mouse whole genome array chips Affy 430_2. The UVR sample served as the control in this preliminary experiment. The results for the combined treatment are expressed relative to the UVR response. Graph 2A shows that the only significantly ($p<0.05$) altered category at level 4 of the Gene Ontology Tree was "epidermal cell differentiation" which is consistent with the histological observations that the keratinizing layer in the epidermis was greatly increased by the terpene in comparison to UVR. Graph 2B shows the results for the down regulated genes. Here 13 categories were significantly ($p<0.05$) down-regulated in the terpene+UVR treatment relative to the UVR only. These down regulations can be attributed to the action of the terpene and include a total of 13 categories of which 5 are strongly associated with the inflammatory reaction, namely: immune system process, inflammatory response, immune response, physiological defense response, and response to wounding. In other words inflammation-relevant genes were strongly down-regulated. The significance of these down-regulations with respect to cancer induction is not clear, but they are consistent with suppression of the sunburn reaction by the terpene.

EXAMPLE 2

Research Design

Experiments will be performed to establish in SKH1 hairless mouse skin how gene expression alterations based on custom expression microarrays, sunburn severity and cancer induction depend on the quantity of the 3 selected terpenes. Preliminary experiments indicated that the terpenes, d-limonene, nootkatone and beta-damascenone given prior to UVR as pure compounds per os in 4 daily 30 microL droplets blocked UVR-induced sunburn. Protocols will be carried out at lower per os terpene concentrations for establishing a dose-response in regard to gene expression alterations, sunburn prevention and cancer prevention.

Table 1 indicates the basic protocol for concentrations of terpenes and doses of UVR to provide baseline information on the changes in gene expression in the SKH1 hairless mouse skin. Adequate levels (80%) of statistical power require generally at least 3 replicates of each exposure group as indicated in Table 1. Practically however it is more cost-efficient to conduct experiments utilizing only 1 chip per 1 mouse. More chips and mice might be needed in special cases where responses are lower, e.g. as the terpenes are diluted. Additionally it may not be necessary to conduct the full protocol as outlined in Table 1 for all 3 terpenes, as the preliminary study indicated the differences between them are small. Where needed, additional replications will provide better estimates of average responses and lower p-values for testing the statistical significance of any differences that may occur.

determined) and one group of UVR only. Each group will contain 30 mice and continue for 26 weeks.

A custom mouse Affymetrix microarray chip containing ~150 keratin- and inflammation-relevant genes identified in the preliminary study will be utilized routinely. Examples of individual genes of special interest are: loricrin, NFKappaB, COX1, COX2, MAPKs, PGE2, ODC, protein kinase C, iNOS, PI3-Akt, TNF, AP1, Nrf2, Keap1 and IKappa kinase. Whole genome mouse microarrays containing 39,000 transcripts with 45,101 probe sets will be utilized selectively in addition to the custom arrays to insure consistent responses at lower terpene concentrations or different entry points. The custom chips are a cost-efficient way of revealing how gene

TABLE 1

Outline of custom microarray experiments - number of mice
Gene expression in mouse skin pretreated daily with terpenes for 4 days prior to UVR exposure.
Tissue samples to be taken 24 h after the UVR exposure.
UVR exposures will be 15 min of solar simulating FS-20 fluorescent lamps (3.0 kJ/m$^2$)

| | Column # | | | | | | | | |
|---|---|---|---|---|---|---|---|---|---|
| Dilution | 1 Control | 2 UVR | 3 Limo. | 4 Limo. + UVR | 5 Noot. | 6 Noot. + UVR | 7 Dama. | 8 Dama. + UVR | Total |
| 10% | 3 | 3 | 3 | 3 | 3 | 3 | 3 | 3 | 24 |
| 50% | 3 | 3 | 3 | 3 | 3 | 3 | 3 | 3 | 24 |
| 100% | 3 | 3 | 3 | 3 | 3 | 3 | 3 | 3 | 24 |

Note:
Limo. = d-limonene,
Noot. = nootkatone,
Dama. = beta-damascenone
*Solvent will be the inactive triglyceride, liponate Based on a combination of sunburn suppression and gene expression alterations, a carcinogenesis experiment will be setup to quantify the degree of cancer prevention that can be expected for a given amount of sunburn suppression and/or gene expression alteration. The carcinogenesis experiment of necessity will be carried out with chronic UVR (0.8 kJ/m$^2$ 3× weekly for 26 weeks) along with a d-limonene supplement (concentration to be determined in relation to gene expression alterations) in the lab chow. Selection of a terpene concentration will be based on custom microarray responses to lab chow supplement with differing concentrations of d-limonene. All experiments will be conducted with skin but tissue from other organs will be preserved for possible future analysis.

The carcinogenesis protocol is designed to include 2 concentrations of d-limonene (not yet categories associated with the suspected terpene mechanism of action vary with terpene concentration.

An initial experiment will be carried out with d-limonene (by a small margin the most potent pure inhibitor of the 3 terpenes) applied as in the preliminary experiment, i.e. 30 µL per os 4 times daily followed by UVR 24 h after the final terpene dose. Tissue sampling for microarray analysis will be performed 24 h after the UVR. At 1 chip per 1 mouse, the per os dilution protocol for d-limonene will require 9 chips and 9 mice (columns 1, 2 and 3 in Table 1. An analogous topical application protocol will require an additional 9 chips and 9 mice. These initial experiments will provide sufficient data to draw conclusions concerning how the gene expression alterations depend on d-limonene concentration and entry mode. An additional 18 mice would be used to evaluate for sunburn suppression at the same d-limonene concentrations. The same

TABLE 2 xxxCarcinogenesis protocol - number of hairless mice
Undiluted d-limonene will be administered once per os 30 µL at times prior to UV irradiation.
UVR exposures will be 15 min of solar simulation FS-20 fluorescent lamps (3.0 kJ/m$^2$)

| Terpene Start Time prior to UVR (d) | Control | UVR only | Limon. | Limon. + UVR | Noot. | Noot. + UVR | Damas. | Damas. + UVR |
|---|---|---|---|---|---|---|---|---|
| 4 | 3 | 3 | 3 | 3 | 3 | 3 | 3 | 3 |
| 6 | 3 | 3 | 3 | 3 | 3 | 3 | 3 | 3 |
| 10 | 3 | 3 | 3 | 3 | 3 | 3 | 3 | 3 |
| 14 | 3 | 3 | 3 | 3 | 3 | 3 | 3 | 3 |
| Total mice | | | | | | 96 | | |

Note:
Limon. = d-limonene,
Noot. = Nootkatone,
Damas. = beta-damascenone protocol will be carried out for beta-damascenone as a second terpene to establish whether potency differences exist between terpenes at lower concentrations. Another experiment will be carried out to determine if the 4 day pre-exposure provides optimal protection. This will involve extending the length of the pre-exposure from 4 d to 10 d and 14 d to establish whether additional protective benefit is available in reference to sunburn prevention (Table 2). If the hypothesis is true that the protective response involves a piling up of keratinocytes and keratin, the signal must occur considerably in advance of the point where the protection becomes effective, because of the need for cell proliferation and the formation of keratin and probably loricrin. Epidermal cell cycle times are generally about 10 days in control epidermis but can be shortened to about 1.5 to 2 days. Still a number of days would be needed to accumulate the cell numbers and keratin mass noted on the histological preparations in the preliminary studies.

Cancer yields are calculated by assigning a number and at death or euthanasia after which histological sections are prepared and evaluated for each tumor. Only histologically verified lesions are scored as malignant neoplasms and assigned to histological type. Available software evaluates cancer yields interactively and projects the response to a pre-chosen standard time point or until a preselected standard deviation is reached. Groups are terminated when standard deviations go below 20% (total tumors=25) of the mean response; a strategy that minimizes caging time and animal per diem fees without compromising precision or conclusions. Based on linear additivity and a Poisson distribution, the cancer yield standard deviations are in the range of 15% to 25%. Accordingly a 50% or greater response difference between groups of 25 animals is detectable with a p-value=0.05 and type 2 error=0.20.

Sample size and statistical analysis by assigning animals to experimental and control groups based on the assumption that at least a 20% difference in tumor yields between control and treatment groups will be obtained. Several factors are considered in the power analysis: (i) the minimum true effect of a treatment, which is regarded as significant; (ii) the standard deviation or random error variance, S2; (iii) the significance level of the statistical test, which is set at a P-value=0.05; and (iv) the power of detecting the true effect of a treatment, P, commonly 0.8. For an expected minimum effect of 20% and a standard deviation of 15%, a minimum sample size of 16 per treatment groups is required to achieve a type 2 error <15%. ANOVA will be used to compare the effect of radiations on body weights in wild-type versus BubR1+/− mice. ANOVA is robust against departure from normality, but non-parametric tests will be utilized as necessary. Additivity will be tested by using the statistical hypothesis that the expected number of tumors per rat is invariant under fractionation of the total dose. The preliminary data for a single fraction of 3 Gy gives an average of 5 cancers per 20 rats. This yields $\lambda 0=0.25$ per rat as the tumor rate. The alternate hypotheses $\lambda 1$ is chosen for a pairwise comparison to be $\lambda 1=\lambda 0 \pm \frac{1}{2}\lambda 0$, so that the absolute difference between alternatives is $|\lambda 1-\lambda 0|=0.125$. The Poisson assumption implies a population standard deviation of $\sigma=(\lambda 0)^{1/2}=0.125$ so that the normalized difference is $|\lambda 1-\lambda 0|/\sigma=1.0$. Consequently the per-group sample size formula for our problem reduces to $N=2(Z1-\sigma/2+Z1-\beta)2$ where the Z's are percentiles of the standard normal distribution corresponding to the significance level $\alpha$ and power $1-\beta$. Because 5 pairwise comparisons will be made, the desired 0.05 significance level is to be adjusted for the individual comparisons by the Bonferroni method, i.e. to use $\alpha=0.05/5=0.01$, and similarly the desired power of 0.80 is to be achieved by using $\beta=(1-0.8)/5=0.05$. Thus $Z1-\sigma/2=Z0.995=2.576$ and $Z1-\beta=Z095=1.645$. Putting this all together the result is that N=36 animals per group.

Results

The data will provide gene expression levels in treated skin in comparison to controls for the terpenes alone and for the UVR alone and then for the various combinations at a time prior to onset of a visible sunburn reaction. These data should provide an immediate indication whether the terpenes produce a consistent change in gene expression patterns and how much the UVR response differs from or is altered by terpenes as concentration changes. In similar experiments in rat skin exposed to ionizing radiation, it was shown that vitamin A, while having no effect on gene expression in controls, blocked about 80% of the inflammation-relevant gene expression alterations caused by the x-rays (Lu et al., *Experimental Biology & Medicine* 232(4):473-480, 2007). In the referenced work the principal effect of the radiation was to activate inflammation-relevant genes in immunocytes that invaded the skin. Something similar is expected in these proposed experiments, although the response to UVR might differ from that of ionizing radiation. Gene expression studies were carried out for d-limonene at 1 hr before the UVR exposure and 1 hour after UVR exposure; the latter being roughly the peak of the inflammatory response in these mice.

Gene expression microarray results will provide insight into how the terpenes are working, because the whole genome mouse chip contains all 39,000 transcripts with 45,101 probe sets in the Affymetrix microarray analysis system. The whole genome chip provides a scan of the entire genome and possibly reveals gene categories associated with all possible suspected mechanisms of action, including proliferative, anti-oxidative and apoptosis genes, etc. In addition the whole genome chips provides information on categories that are not yet suspected of involvement in cancer prevention, as well as, information on responses of individual genes, such as, NFKappaB, COX1, COX2, MAPKs, PGE2, ODC, protein kinase C, iNOS, PI3-Akt, TNF-$\alpha$, AP1, Nrf2, Keap1 and IKappa kinase. The important point here is that these scans permit identification of categories of genes and even possibly individual genes as putative biomarkers in tumor prevention. Once such genes are identified by the genome chips, custom arrays will be fabricated and utilized at much lower expense. The data on comparative oxidative stress levels as quantified by 8-oxo-dG levels and the incidence of apoptosis quantified by the TUNEL assay will be available and should provide confirmation for the gene expression responses to some extent. Certainly establishing any one of these endpoints as putative tumor prevention markers would be a positive contribution from these studies.

Likely, the terpenes will bind to the cell membrane receptors without a threshold, i.e. the relationship between terpene concentration and sunburn or cancer prevention should monotonically increase with terpene concentration possibly plateauing at the higher levels as a possible scenario. Several studies have shown that terpenes are capable of causing direct cellular responses, such as apoptosis induction and anti-oxidation in vitro which supports the idea that terpenes can interact directly with cells. Possibly 2 mechanisms are acting independently, one based on systemic responses and one based on a direct interaction between epithelial cell and terpene. It is well-established that TPA, a terpene, acts in vitro by binding directly to protein kinase C (Wu et al., *Proceedings of the National Academy of Sciences of the United States of America* 101(18):7094-7099, 2004; Borek, C. Integrative Cancer Therapies 3(4):333-341, 2004).

Methods and Procedures:
UV Irradiation Technique

Mice will be irradiated with a bank of four parallel Westinghouse solar-spectrum FS-20 fluorescent lamps either once at a dose of 3.0 kJ/m² for short term protocols or 3 times per week at a dose of 1.0 kJ/m² for long-term carcinogenesis protocols. The UVR dose rates will be measured with a calibrated IL 1400A digital radiometer/photometer equipped with a SEL240 UVB-1 detector (International Light, Inc.). The UVR fluence is 0.2 kJ/m²/min and 1.0 kJ/m² is approximately 30% of the minimal erythemic dose (MED) for these mice.

Diets

Initially terpenes will be administered per os via pipette. If needed for final testing, cereal-based diets will be formulated with equivalent terpene concentrations and supplied as a powder containing designated terpenes prepared by Dyets, Inc., Bethlehem Pa. Chemicals will be purchased from Sigma Biochemical, St. Louis, Mo. The experimental concentrations of terpenes are expected to be non-toxic to mice. Terpenes were a gift from Biokeys for Flavors, LLC, Norwood, N.J.

Gene Expression Microarray Analysis for Keratinocytes and Skin Samples

RNA will be extracted from a 0.1 g sample of mouse skin and an equal quantity of keratinocytes by using the TRIZOL reagent (Invitrogen, Carlsbad, Calif., USA) according to the manufacture's instructions and 200 μg of total RNA will be used for the isolation of poly A+ mRNA by using Oligotex mRNA mini columns (QIAGEN, Valencia, Calif., USA). The final centrifugation will be performed after the incubation with 1/10 volume of 3.0 M NaOAc, 2.5 volumes of ethanol and 1 μl glycogen (Boehringer Mannheim GmbH, Mannheim, Germany) at −20° C. overnight. Then the pellet will be resuspended in diethylpyrocarbonate (DEPC)-treated water. RNA will be labeled with biotin and hybridized to a Mouse genome 430_2 GeneChip® microarray (Affymetrix, Inc. Santa Clara, Calif., USA). Data from the Affymetrix mouse expression array chip are imported into the BRB-ArrayTools Version 3.3.0 developed by the Biometric Research Branch of the U.S. National Cancer Institute for normalization and analysis. Statistical comparison between the treated group and control group based on 3 replicates each was performed by using the class comparison tool of BRB Array Tool software, which uses two sample T-tests (with random variance model) to find genes whose expression varied significantly, a value of $P \leq 0.001$ was chosen as statistically significant. In order to identify significantly altered categories of genes, the Gene Ontogeny website will be utilized as documented in the GOTree Machine software suite. A list of significantly altered genes derived from the BRB-ArrayTools software will be uploaded into the GOTree software for derivation of significantly altered gene categories. For these calculations the entire list of genes on the Affymetrix (mouse 430-2) microarray will be used as the reference list.

EXAMPLE 3

Experiments will be performed to quantify in SKH1 mouse skin 2 separate types of DNA damage, direct and oxidative, in epithelial cell DNA following the same exposure protocols for UVR and terpenes as described in Aim #1. Cyclobutyl pyrimidine dimers (CPDs) and 8-oxo-dG will be utilized as a measure of direct UVR-induced DNA damage and oxidative DNA damage respectively. With the results from Aim #1, these data will prove whether or not terpene-induced UVR absorption is the basis for sunburn and cancer preventive activity.

These experiments are based on the endpoint of induction of cyclobutyl pyrimidine dimers (CPDs) in the DNA of skin epithelial cells by UVR. Preliminary experiments have shown that inflammation genes induced by UVR can be blocked by each of 3 terpenes, d-limonene, nootkatone and beta-damascenone, administered per os daily for 4 days in 30 microL droplets prior to irradiation. Female SKH1 hairless mice will be exposed to the solar spectrum UVR for 15 minutes at a distance of 20 cm from a bank of 4 FS-20 fluorescent lamps. Typically inflammation reaches a peak between 3-6 days after the UVR exposure.

TABLE 3

Protocol for CPDs, 6,4 PPs, 8-oxo-dG and TUNEL assays - number of mice
Mouse skin pretreated daily with a terpene for 4 days prior to UVR exposure.
Tissue samples to be taken 24 h after the UVR exposure.
UVR dorsal skin exposure: 15 min of solar simulating FS-20 fluorescent lamps (3.0 kJ/m²)

| | Column # | | | | | | | | |
|---|---|---|---|---|---|---|---|---|---|
| Dilution* | 1 Control | 2 UVR | 3 Limo | 4 Limo. + UVR | 5 Noot. | 6 Noot. + UVR | 7 Dama. | 8 Dama. + UVR | Total |
| 1/10 | 3 | 3 | 3 | 3 | 3 | 3 | 3 | 3 | 24 |
| 1/2 | 3 | 3 | 3 | 3 | 3 | 3 | 3 | 3 | 24 |
| 1/1 | 3 | 3 | 3 | 3 | 3 | 3 | 3 | 3 | 24 |

Note:
Limo. = d-limonene,
Noot. = nootkatone,
Dama. = beta-damascenone
*Solvent will be the inactive triglyceride, liponate Oxidative stress levels in the form of 8-oxo-dG in the skin epithelium will be measured every other day for 6 days after UVR exposure either with or without supplementary terpenes prior and subsequent to the UVR. The protocol is designed to establish at what approximate concentration each terpene loses its effectiveness as a sunburn retardant. PCNA procedures will be carried out on skin tissues obtained in these experiments to confirm that proliferative responses are occurring as expected. Occasional tunel assays will be carried out to monitor apoptosis during and after the various exposures. These results will be important for confirming the timing of gene expression via microarray analysis might be needed to confirm when local gene expression signals are altered in relation to the administration of the terpenes. These experiments are designed for assaying all 3 terpenes, but d-limonene will be tested initially. The other terpenes might be tested later for confirmatory purposes.

Initial experiments will involve d-limonene. Each of the following assays will be carried out on skin tissue obtained from 4 different locations on each mouse. The assays are: CPDs, PCNA, 8-oxo-dG and TUNEL. The 6,4 photoproduct assay will on occasion be carried out as an adjunct to the CPD assay, because they are somewhat redundant although their repair rates in mouse skin differ markedly. The photolesions will be an objective measure of the amount of UVR that has penetrated to the cutaneous epithelium. Selective localization of the photoproducts will be pursued by using an in situ procedure an approach to identifying epithelial cells with the greatest cancer risk for comparison with carcinogenesis studies. The 8-oxo-dG assay will provide information to verify that inhibition of inflammation-relevant genes by the terpene produces measurable reductions of localized oxidative stress as assumed.

The results of experiments will provide exact 1:1 comparisons. Tissue sampling will be performed 24 h after the UVR. At 4 assays per 1 mouse, the per os dilution protocol will require 36 assays on 9 mice. An analogous topical application protocol will require an additional 9 mice. These initial experiments could possibly provide sufficient data to draw conclusions concerning how the gene expression alterations are related to the various objective endpoints for d-limonene. The same protocol will be carried out for beta-damascenone as a second terpene to establish whether potency differences might exist between terpenes at lower concentrations and whether comparisons with gene expression results are consistent or at variance.

Results

The CPDs with backup from 6,4 PPs will establish the comparative amount of UVR getting to the cutaneous epithelial cells in relation to dose and type of terpene. However as both assays are immune-based and immune-based methods can vary, redundancy should be accepted as an advantage until proven otherwise. Recent studies of the carcinogenic enhancement of UVR in mouse skin by arsenic in the drinking water indicates that the combination of DNA photodamage by the UVR and oxidative DNA damage in the form of 8-oxo-dG by the arsenic causes nearly a 5-fold synergistic increase in the yield of squamous carcinomas; a co-carcinogenic effect. If so even a small reduction of the oxidative stress by the terpene might produce a substantial reduction in the yield of cancer, if sunburn and cancer are as closely linked as is generally believed. Because other documented effects of terpenes includes increased proliferations and apoptosis, the PCNA and TUNEL assays will be performed selectively as a backup to the possibility that oxidative stress levels may not be a consistent biomarker of sunburn and/or skin cancer inhibition by the terpenes.

The prevention of sunburn by the terpene will induce epidermal differentiation (keratinization) genes that absorb the UVR which will be apparent in the results as a reduction in the CPDs and/or 6,4 PPs. In addition the custom microarrays will confirm that inflammation genes were down-regulated by the terpene and that will be quantified as a reduction in the level of 8-oxo-dG in the epithelial DNA. In this way gene expression changes would be verified independently, and it might even be possible to make use of carcinogenesis data to predict the degree of cancer prevention to be expected from a given combination of lower DNA photodamage and lower oxidative stress levels.

Methods and Procedures

Oxidative DNA Damage in Skin of Mice (8-oxo-dG)

Mouse DNA will be extracted from 100 mg or larger samples of tissue by using the DNA isolation kit from Roche Diagnostics Corporation (Indianapolis, Ind.). The DNA will be dissolved in AE elution buffer (Qiagen, Valencia, Calif.), and 100 µg will be digested as described previously. The following incubations will be performed: DNase I for 30 min at 37° C.; NP1 for 60 min at 37° C.; AP for 30 min at 37° C.; and phosphodiesterase inhibitors PDEI and PDEII for 30 min at 37° C. The incubation mixture will be filtered through a 0.5 ultrafree centrifugal filter (Millipore, Billerica, Mass.). The iron chelator DTPA will be added to the DNA hydrolysates to prevent artificial oxidation. Twenty µl of hydrolysate will be analyzed by high-performance liquid chromatography. The high-performance liquid chromatography with electron capture detection system consisted of an Agilent 1100 binary pump, autosampler, and variable wavelength detector controlled by Chemstation Software 7.01 (Agilent Technologies, Palo Alto, Calif.); an ESA Coulochem II electrochemical detector (ESA, Inc., Chelmsford, Mass.); a C18 Alltima guard column, 7.5×4.6 mm, particle size of 5 µm (Alltech, Deerfield, Ill.); and a YMC ODS-AQ column, 4.6×15 cm, 120 Å, S-5 (Waters Corporation, Milford, Mass.). The mobile phase consisted of 8% aqueous methanol containing 50 mM sodium acetate buffer (pH 5.2). Elution will be isocratic at a flow rate of 0.8 ml/min. The deoxyguanosine concentration will be monitored based on absorbance (245 nm), and 8-oxo-dG concentration will be based on the electrochemical reading (400 mV). Levels will be quantified using the standard curves, of each compound. The degree of DNA damage will be expressed as 8-oxo-dG per $10^6$ deoxyguanosine.

Quantitation of UV Photoproducts by Enzyme-Linked Immunosorbent Assay (ELISA)

After UV-irradiation or after subsequent DNA repair, genomic DNA is purified from the keratinoctes isolated from mouse epidermis and is heat-denatured. Polyvinylchloride flat-bottom microtiter plates (Dynatech, Alexandria, Va.) pre-coated with 1% protamine sulfate (Sigma) is then incubated with mouse genomic DNA at 37° C. for 20 hour. After drying, the plates are washed 5 times with PBS containing 0.05% Tween 20 (PBS-T). The plates are then incubated with 1% goat serum in PBS (150 µl/well) at 37° C. for 1 hr to prevent non-specific binding of the antibody and washed again. 100 µl of the 6,4 photoproduct or cyclobutyl pyrimidine dimer (CPD) antibody (generously provided by Dr. Toshio Mori) are added to each of 3 wells and incubated at 37° C. for 30 min. The plates are washed 5 times with PBS-T and then incubated with 100 µl of a biotin-F(ab)$_2$ fragment goat anti mouse IgG(H+ L) (1/2000 in PBS, Zymed) at 37° C. for 30 min. The plates are washed 5 times with PBS-T and then incubated with 100 µl of streptavidin conjugated with peroxidase (1/10000 in PBS, Zymed) at 37° C. for 20 min. After 3 washings with PBS-T and 2 subsequent washings with citrate-phosphate buffer (pH 5.0), 100 µl of substrate solution consisting of 0.04% o-phenylene diamine and 0.007% $H_2O_2$ in citrate-phosphate buffer is added to each well. Following 30 min incubation at 37° C., 50 µl of 2M $H_2SO_4$ is added to stop the reaction, and absorbance at 492 nm is measured by using an HTS 7000 Bio Assay Reader (Perkin Elmer). Standard curves are obtained from DNA samples extracted immediately after UV irradiation.

In Situ Visualization of CPD and PCNA

Two monoclonal antibodies, TDM-2 for CPD (and 64-M2 for 6,4 PPs, if needed), will be used for visualizing of UV induced DNA damage. The specificity of these antibodies has been examined in detail, no detectable crossreactivity was found between CPD and 6,4 PPs. Skin biopsies cut as 4-µM thick cryosections are fixed with 0.001% paraformaldehyde for 3 min at 4° C. and dehydrated through a graded methanol series. Sections are microwaved (500 W) for a total of 5 min in 10 mM citrate buffer, pH 6.0, and are then treated with 0.1% trypsin for 30 min at room temperature. Slides are subsequently treated with 0.07 M NaOH in 70% ethanol for 15 min at room temperature to denature DNA. After blocking and RNase A treatment, slides are incubated with TDM-2 at 1:10,000 dilution or with 64M-2 at 1:1,500 dilution with 5% fetal bovine serum at 4° C. overnight. The binding of monoclonal antibodies to respective photolesions in each nucleus can be detected with a biotin-streptavidin system and FITC. The nuclei are then counterstained with propidium iodide. For double staining of CPD and PCNA, a PCNA monoclonal antibody (Clone 24, Transduction Laboratory, Lexington, Ky.) at 1:50 dilution is used and denaturation of DNA is omitted. The dishes are washed with phosphate-buffered saline, mounted in drops of ProLong Antifade (Molecular Probes, Eugene, Oreg.), and coverslipped. Fluorescent images are obtained by using an InSIGHTplus-IQ laser-scanning confocal microscope (Meridian Instruments, Okemos, Mich.).

Assay of DNA Fragments as Indicator of Apoptosis (TUNEL Assay)

The TUNEL (terminal deoxynucleotide transferase {TdT}-mediated digoxigenin-uridine triphosphate {dig-UTP} nick-end labeling which measures 3'-hydroxyl ends of DNA fragments formed during programmed cell death, i.e. apoptosis. Apoptotic cells are detected using the DeadEnd Colorimetric TUNEL system (Promega, Madison, Wis.) following manufacturer's protocol with some modifications. The tissue is fixed in 1% paraformaldehyde, then sectioned at 6 microns and processed according to the Apop Tag-Fluorescein (Oncor, Inc., Gaithersburg, Md.) protocol (55). Briefly the slides are incubated first with TdT and dig-UTP and then with fluorescein isothiocyanate (FITC)-labeled anti-digoxigenin antibody (anti-dig-FITC). The slides are then washed with Triton X-100 and counterstained with 5 ug/ml propidium iodide. Cells are then observed with a fluorescent microscope and measurements are made of the relative green or red fluorescence by using the appropriate band pass filters and a photometer. About 100 cells will be quantified to establish the average ratio. Sections are mounted after dehydration and observed under 400× magnification for TUNEL-positive cells.

Female hairless (SKH1) mice will be utilized in the proposed work for 2 purposes: 1) to establish comparative gene expression patterns and cancer induction in skin for different doses of per os or topical exposure to 3 terpenes (d-limonene, nootkatone, and beta-damascenon) prior to UVR and 2) for evaluating the comparative yields of direct DNA damage (CPDs and 6,4 photoproducts) versus oxidative DNA damage (8-oxo-dG) in mouse skin exposed to terpenes and UVR as in 1). The work addresses the question whether the cancer preventive properties of the terpenes depend on whole body exposure or direct chemical interactions in skin. Approximately 190 mice will be needed over the full study including mice to establish the effect of the terpenes on gene expression alterations, anti-oxidative levels and apoptosis incidence. Where required lab chow diets will be formulated and supplied as a powder containing designated terpenes at specified concentrations by Dyets, Inc., Bethlehem Pa. Chemicals will be purchased from Sigma Biochemical, St. Louis, Mo. The proposed concentrations and entry routes of terpenes are not expected to produce toxicity in SKH1 mice.

These experiments require the induction of malignant (squamous carcinomas) and benign (papillomas) neoplastic lesions in the skin of SKH1 mice. No in vitro system or theoretical approach is currently available that could provide reliable information as a surrogate for tumor induction in animals. The anti-carcinogenic effectiveness of terpenes acting through direct or indirect pathways is a poorly understood phenomenon and findings from in vitro studies would not be persuasive in comparison to equivalent results obtained in animals.

Veterinary care is provided by the School of Medicine animal facility. A veterinarian visits the facility once per month on a routine basis and more frequently if special needs arise. The facility was within the last year partially converted from conventional to a barrier facility, but this study will not use the barrier. The animals will be checked daily for overt signs of illness and mortality. Each batch of new animals will be quarantined for 8 weeks, during which time they are observed for signs of overt illness and abnormalities. Sentinel mice are periodically culled and complete serological, bacteriological, parasitological and pathological examinations are performed by animal care personnel. Only if the sentinels are completely free of disease and abnormalities will experimentation commence on the quarantined animals.

It is not expected that any procedures to be employed in the proposed experiments will produce pain or distress to the mice not relieved by appropriate analgesia or anesthesia. The use of animals is essential for these studies, since the protocols involve cancer induction. The animals will have ad libitum access to food and water. Fresh food is supplied twice weekly, and excreta are removed twice weekly. The racks and cages are cleaned every two weeks. Cages will be placed on wheeled racks in conventional, well ventilated (12-15 changes per hour) animal room kept at 22+/−2° C. and 55+/−15% relative humidity, and lighted on a 12 hour/day timer. The animals will be checked daily for overt signs of illness and mortality. Moribund animals will be euthanized by $CO_2$ asphyxia. The cereal-based diet adequate in all essential nutrients will be purchased from Purina Inc. Mice will be fed 3 times per week. Sentinel mice kept with each experiment are examined periodically and at the termination of the experiment, when complete serological, bacteriological, parasitological and pathological examinations are performed. The N.Y.U. Medical Center Animal Facilities are registered with and approved by the US Department of Agriculture (21-118). The I.E.M. Animal Facility and all experimental protocols are subject to approval of the N.Y.U. Medical Center IACUC, while animal care and maintenance, including housing, are conforming to the NIH Guide for the Care and Use of Laboratory, and the facility is AALAC accredited.

The method of euthanasia will be i.p. injection with 120 mg/kg of body weight of sodium pentobarbital or $CO_2$ inhalation depending on the assay being performed. Both methods are approved by the Panel on Euthanasia of the American Veterinary Medical Association.

It will be apparent to those of skill in this art that the foregoing examples are only illustrative of the present invention and that modifications and additions are apparent to those of skill in the art. All such modifications and additions are included within the scope of the present invention, which is to be limited only by the scope, including equivalents, of the following, appended claims.

We claim:

1. A method of increasing the amount of ultraviolet radiation (UVR) that the skin can block or absorb comprising administering a terpene wherein the terpene is administered prior to exposure to UVR.

2. A method according to claim 1 wherein the terpene is administered at least one time per day.

3. A method according to claim 1 wherein the terpene is selected from the group consisting of beta-damascenone, nootkatone, and d-limonene.

4. A method according to claim 1 wherein the terpene is administered orally.

5. A method according to claim 1 wherein the terpene is administered topically.

6. A method according to claim 1 wherein the terpene is administered in a dosage and in amounts sufficient to reduce the amount of cutaneous inflammation and erythema present in the skin of subjects receiving the terpene compared to the amount of cutaneous inflammation and erythema present in the skin of subjects not receiving the terpene when both subjects or both sets of subjects are exposed to the same dosage of UVR.

7. A method according to claim 1 wherein the terpene is administered in a dosage and in amounts sufficient to increase epidermal cell proliferation and increase keratin production in the skin of subjects receiving the terpene compared to the amount of epidermal cell proliferation and keratin production present in the skin of subjects not receiving the terpene when both subjects or both sets of subjects are exposed to the same dosage of UVR.

8. A method according to claim 1 wherein the terpene is administered in a dosage and in amounts sufficient to alter the expression of one or more gene products selected from the group consisting of NFKappaB, COX1, COX2, MAPKS, PGE2, ODC, protein kinase C, INOS, PI3-AKT, TNF-A, AP1, NRF2, KEAP1 and IKappa kinase.

9. A method of increasing the amount of ultraviolet radiation (UVR) that the skin can block or absorb comprising orally administering a terpene.

10. A method of increasing the amount of ultraviolet radiation (UVR) that the skin can block or absorb comprising administering a terpene in a dosage and in amounts sufficient to increase epidermal cell proliferation and increase keratin production in the skin of subjects receiving the terpene compared to the amount of epidermal cell proliferation and keratin production present in the skin of subjects not receiving the terpene when both subjects or both sets of subjects are exposed to the same dosage of UVR.

11. A method of increasing the amount of ultraviolet radiation (UVR) that the skin can block or absorb comprising administering a terpene in a dosage and in amounts sufficient to alter the expression of one or more gene products selected from the group consisting of NFKappaB, COX1, COX2, MAPKS, PGE2, ODC, protein kinase C, INOS, PI3-AKT, TNF-A, AP1, NRF2, KEAP1 and IKappa kinase.

12. A method of increasing the amount of ultraviolet radiation (UVR) that the skin can block or absorb according to claim 1 wherein the terpene is a hydrocarbon having an isoprene group.

13. A method of increasing the amount of ultraviolet radiation (UVR) that the skin can block or absorb according to claim 1 wherein the terpene is administered orally at least one hour prior to exposure to the sun or UV radiation.

* * * * *